(12) United States Patent
He et al.

(10) Patent No.: US 8,445,662 B2
(45) Date of Patent: May 21, 2013

(54) MYCOBACTERIUM TUBERCULOSIS FUSION PROTEIN AND USES THEREOF

(75) Inventors: Xiuyun He, Beijing (CN); Yuhui Zhuang, Beijing (CN); Haibin Wang, Guangdong (CN); Jianhua Tao, Beijing (CN)

(73) Assignees: The 309th Hospital, The People's Liberation Army, Beijing (CN); Yangzhou Yilin Biotechnology Co., Ltd, Yangzhou (CN)

( * ) Notice: Subject to any disclaimer, the term of this patent is extended or adjusted under 35 U.S.C. 154(b) by 0 days.

(21) Appl. No.: 13/446,098

(22) Filed: Apr. 13, 2012

(65) Prior Publication Data

US 2012/0258129 A1 Oct. 11, 2012

Related U.S. Application Data

(62) Division of application No. 12/160,280, filed as application No. PCT/CN2007/000087 on Jan. 10, 2007, now Pat. No. 8,173,773.

(30) Foreign Application Priority Data

Jan. 10, 2006 (CN) .......................... 2006 1 0000710

(51) Int. Cl.
*C12N 1/20* (2006.01)
*C12N 15/00* (2006.01)
*C12P 21/06* (2006.01)

(52) U.S. Cl.
USPC ... 536/23.7; 435/69.1; 435/252.3; 435/253.1; 435/320.1

(58) Field of Classification Search
None
See application file for complete search history.

(56) References Cited

U.S. PATENT DOCUMENTS

| | | | |
|---|---|---|---|
| 5,169,940 | A | 12/1992 | Patarroyo |
| 5,364,934 | A | 11/1994 | Drayna et al. |
| 6,592,877 | B1 | 7/2003 | Reed et al. |
| 6,596,281 | B1 | 7/2003 | Gennaro et al. |
| 2002/0098200 | A1 | 7/2002 | Campos-Neto et al. |
| 2002/0176867 | A1 | 11/2002 | Andersen et al. |
| 2004/0087782 | A1* | 5/2004 | Tsuchiya et al. ............. 536/23.1 |
| 2005/0118201 | A1 | 6/2005 | Wright et al. |

FOREIGN PATENT DOCUMENTS

| | | |
|---|---|---|
| CN | 1241212 | 1/2000 |
| CN | 1241212 A | 1/2000 |
| CN | 1737153 A | 2/2006 |
| CN | 1793367 A | 6/2006 |
| JP | 2003-510370 A | 3/2003 |
| WO | 9501441 A1 | 1/1995 |
| WO | 98/16645 A | 4/1998 |
| WO | 9942076 | 8/1999 |
| WO | 0124820 A | 4/2001 |
| WO | 0204018 A | 1/2002 |
| WO | 0204018 A2 | 1/2002 |
| WO | 02072792 | 9/2002 |
| WO | 2004006952 A | 1/2004 |
| WO | 2005061534 A | 7/2005 |

OTHER PUBLICATIONS

Quan Chen; "Construction of a prokaryotic expression vector carrying MTB lhp-esat6 fusion gene and the use of the recombinant CFP10-ESAT6 fusion protein"; Dissertation for the degree of doctor at Chongqing Medical University; May 2003; China.
Gang Liu, et al; "Development of Proteomics Research of Mycobacterium tuberculosis"; Foreign Medical Sciences (Section of Biologics for Prophylaxis, Diagnosis and Therapy); Feb. 2005; pp. 18-20 and 23; vol. 28 No. 1; China.
Baily GV, et al, Ind. J. Med. Res., 72:1-74,1980.
Brandt L., et al. Infect. Immun., 70:672-678, 2002.
Guo L, et al. Chinese Journal of Coal Industry Medicine, 3(9):940-941, 2000.
Infante E, et al. Clinical and Experimental Immunology, 141:21-28, 2005.
Sampson SL, et al., Infect. Immun., 72:3031-3037, 2004.
Sugawara I, et al., Tuberculosis. 83:331-337, 2003.
Roberts A.D. et al, Immunology, 85:502-508, 1995.
Olsen AW, et al, Infect. Immun., 72:6148-6150, 2004.
Cai H, et al, Vaccine, 23:3887-3895, 2005.
Langermans JAM, et al. Vaccine, 23:2740-2750, 2005.
Olsen AW, et al., Infect. Immun., 69:2773-2778, 2001.
Cunningham and Wells Science. 244:1081-1085, 1989.
Chothia, J.Mol.Biol., 105:1-14, 1976.
Lin X, et al., Modern Cellular and Molecular Immunology, 1-11, 1999.
Orme IM, et al. J. Infect Dis, 167:1481-1497, 1993.
Andersen P, et al., J. Immunol, 154:3359-3372, 1995.
Flesch IE, et al. Infect. Immun., 58:2675-2677, 1990.
Li Z, et al, A New Generation of Vaccine, 221-222, 2001.
Kamath AT, et al, Infect. Immun., 67:1702-1707, 1999.
Cooper AM, et al. J Exp. Med., 178:2243-2247, 1993.
Cooper AM, et al., J Exp. Med., 186:30-45, 1997.
Flynn JL, et al., Proc. Natl. Acad. Sci. USA 89:12013-12017, 1992.
Tascon RE, et al. Infect. Immun., 66:830-834, 1998.
Chan J, et al. Clinical Immunol., 110:2-12, 2004.
Miller, et al. Infect. Immun., 72:2872-2878, 2004.
Oka H, et al., Immunol. Letters, 70:109-117, 1999.
Ausubel, et al. Current Protocols in Molecular Biology, Chapter 7, John Wiley & Sons, Inc. 1999.
Sambrook, et al., Molecular Cloning: A Laboratory Manual, Cold Spring Harbor Press, 2001.
Cohen SN, et al, PNAS,69:2110-2114, 1972.
Mandel M. et al., Journal of Molecular Biology, 53:159-162, 1970.
Kita Y, et al., Vaccine, 023:2132-2135, 2005.
Sable, et al. (Clinical Immunology vol. 122, pp. 239-251, 2007).
Plotkin, et al. (Vaccines WB Saunders Co., p. 571, 1988).

(Continued)

*Primary Examiner* — Albert Navarro
(74) *Attorney, Agent, or Firm* — Lucas & Mercanti, LLP

(57) ABSTRACT

The present invention is related to a *M. tuberculosis* fusion protein, polynucleotide coding for said protein, and a vector and host cell that contain said polynucleotide. The present invention also involves the preparation of said fusion protein, and the use thereof in preventions and treatment of tuberculosis.

7 Claims, 8 Drawing Sheets

OTHER PUBLICATIONS

Avi-Hai Hovav, et al. Gamma Interferon and Monophosphoryl Lipid A-Trehalose Dicorynomycolate Are Efficient Adjuvants for Mycobacterium tuberculosis Multivalent Acelluar Vaccine, Infection and Immunity, Jan. 2005, p. 250-257, vol. 73, No. 1, American Society for Microbiology.

V. Rao, et al, Modulation of Host Immune Responses by Overexpression of Immunodominant Antigens of Mycobacterium tuberculosis in Bacille Calmette-Guerin, Scandinavian Journal of Immunology 58, 2003, p. 449-461, Blackwell Publishing Ltd.

Yolanda Lopez-Vidal, et al. Response of IFN and IgG to ESAT-6 and 38 kDa Recombinant Proteins and their Peptides from Mycobacterium tuberculosis in Tuberculosis Patients and Asymptomatic Household Contacts May Indicate Possible Early-Stage Infection in the Latter, Archives of Medical Research, 2004, p. 308-317, 35, Elsevier, Inc.

Fang Chee-Mun et al.: "Cloning, expression, and purification of recombinant protein from a single synthetic multivalent construct of Mycobacterium tuberculosis", Protein Expression and Purification, vol. 47, No. 2, Jun. 2006, pp. 341-347, XP002523453, ISSN: 1046-5928.

* cited by examiner

1 Rdna marker     2 p38-10
NcoI+HindIII     3 P38-10
BamHI+HindIII     4 P38-10
NcoI+BamHI     5 P38-10 BamHI
6 P38 NcoI+BamHI     7 p38 BamHI
8 100 bp ladder

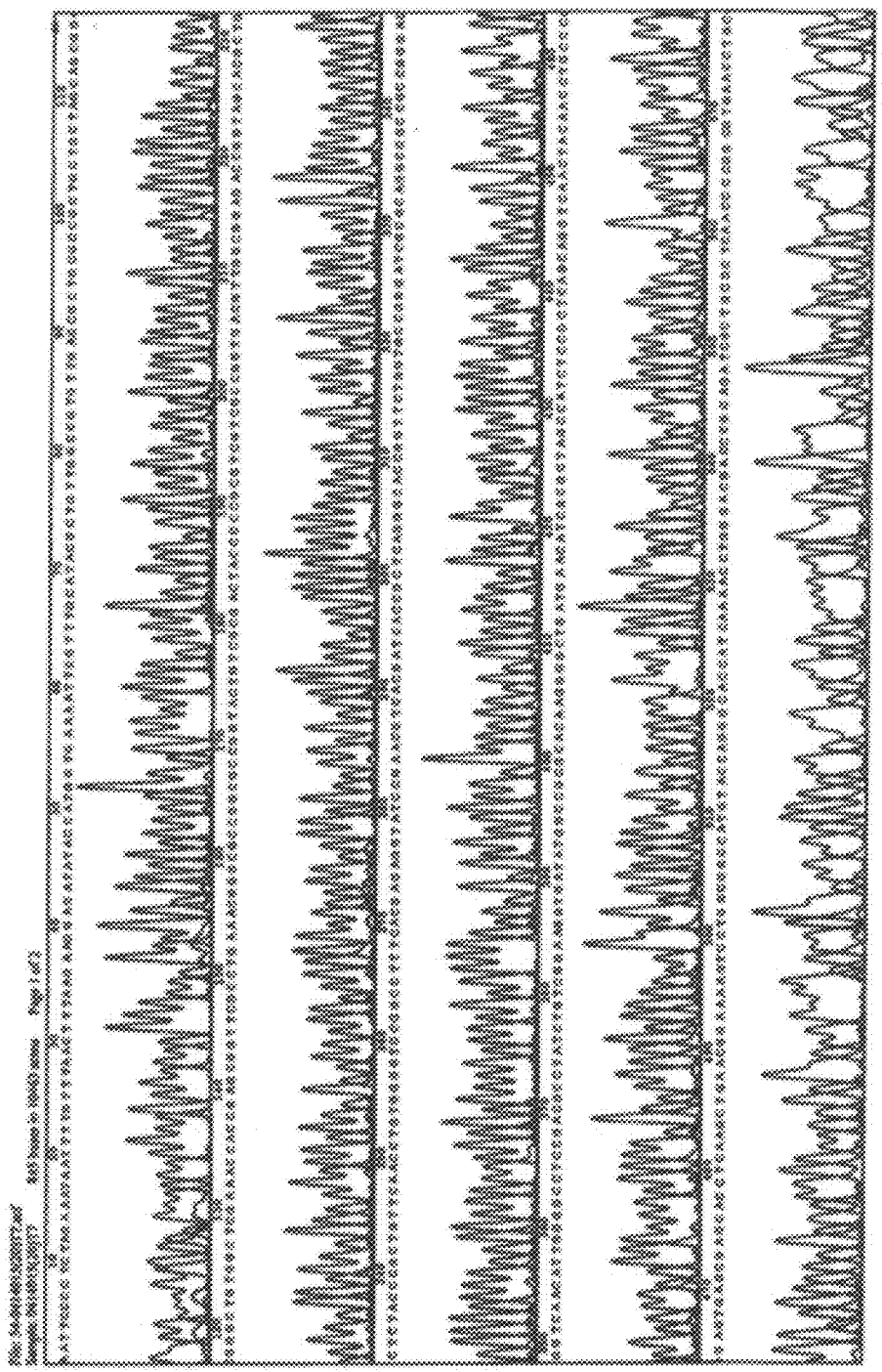
Fig. 2 Sequencing in forward direction

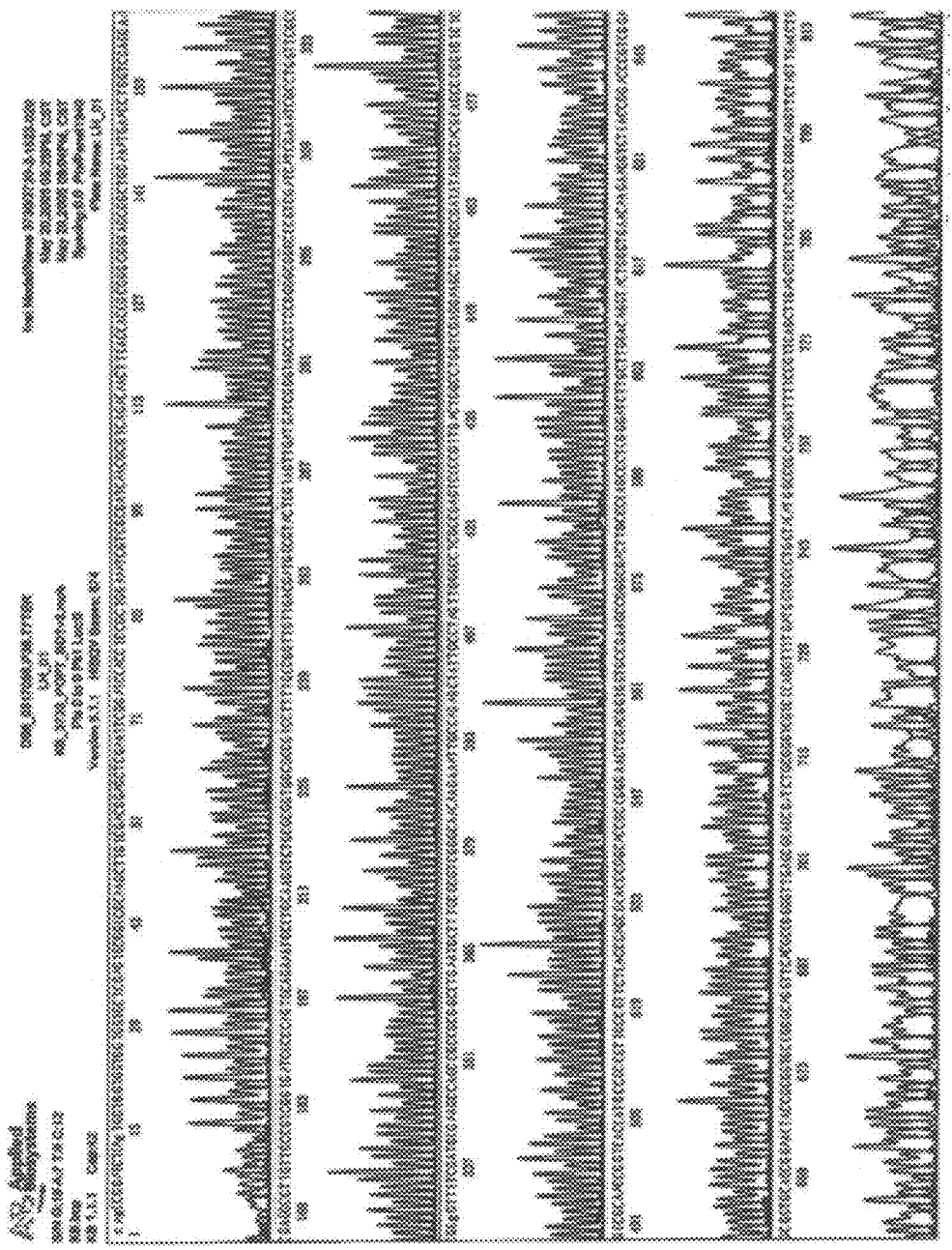
Fig.2 (continued 1) Sequencing the reverse complementary chain

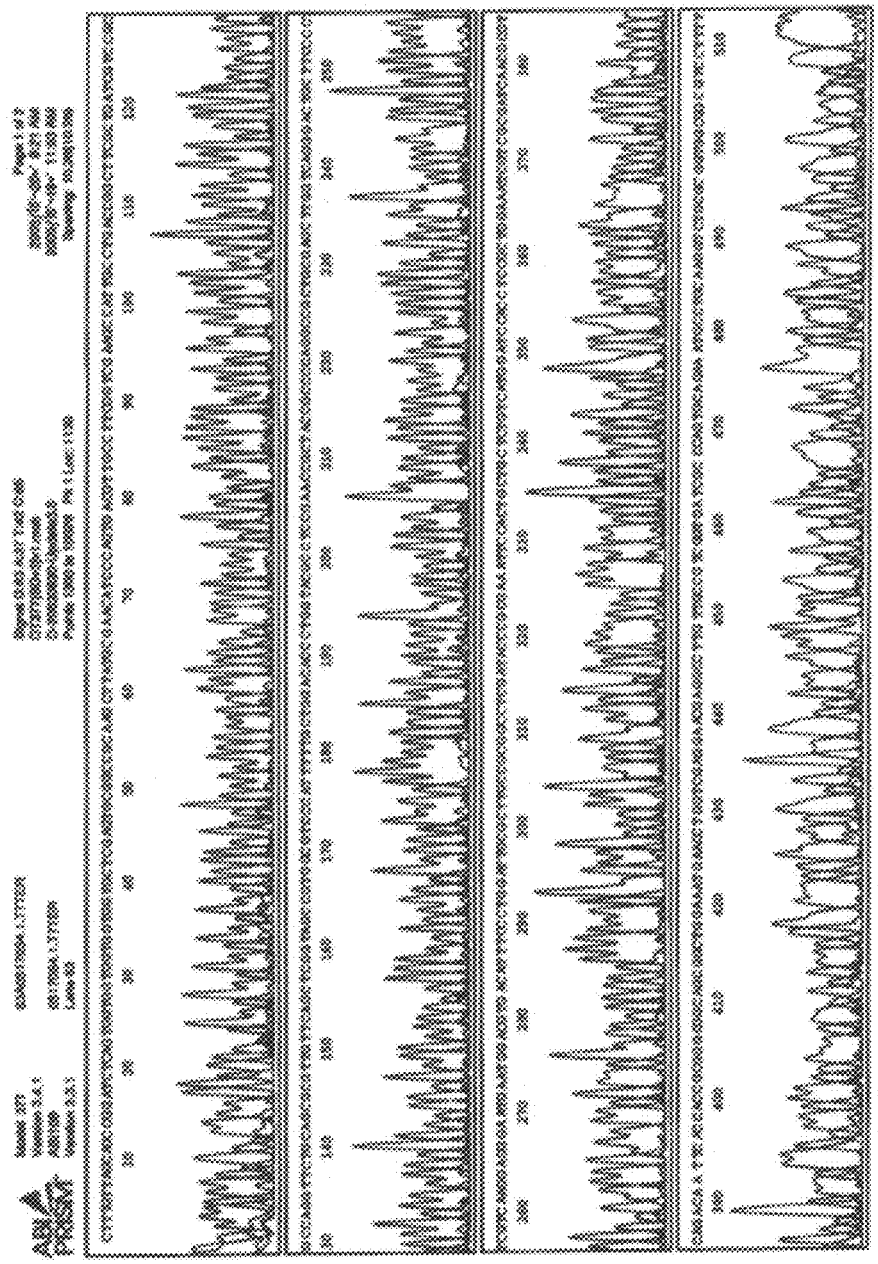
Fig.2 (continued 2) Sequencing the reverse complementary chain p38-10/BL21 (DE3) host bacteria induced by 1-9 different concentrations of IPTG (in sequence: 2, 1.4, 1.2, 1.0, 0.8, 0.6, 0.4, 0.2, 0)
10 Molecular weight of protein 1 protein marker
2 no loading
4, 5, 7 and 8 recovered protein by second running through the purification column
6 recovered protein by first running through the purification column

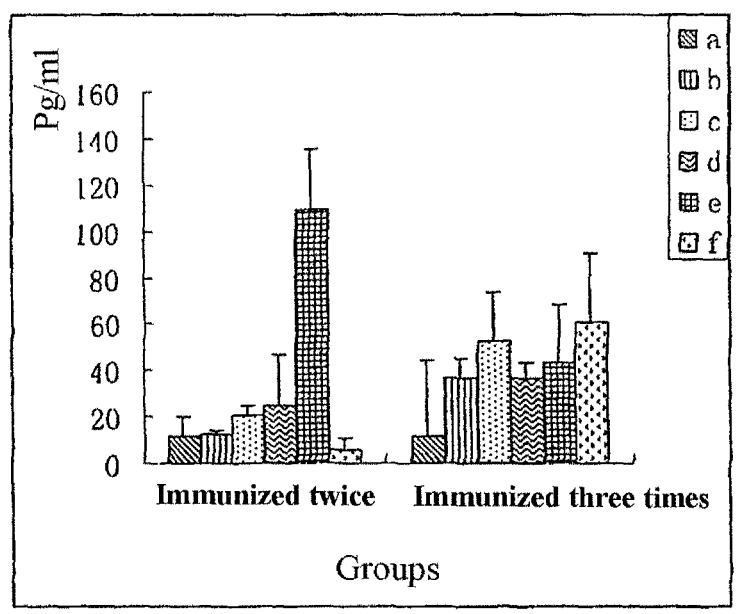
Fig. 6 Secreted IFN-γ by mouse spleen T cell

SEQUENCE LISTING

```
<160> NUMBER OF SEQ ID NOS: 12

<210> SEQ ID NO 1
<211> LENGTH: 1125
<212> TYPE: DNA
<213> ORGANISM: Mycobacterium tuberculosis
<220> FEATURE:
<221> NAME/KEY: CDS
<222> LOCATION: (1)..(1125)

<400> SEQUENCE: 1 gtg aaa att cgt ttg cat acg ctg ttg gcc gtg ttg acc gct gcg ccg      48
Val Lys Ile Arg Leu His Thr Leu Leu Ala Val Leu Thr Ala Ala Pro
1               5                   10                  15 ctg ctg cta gca gcg gcg ggc tgt ggc tcg aaa cca ccg agc ggt tcg      96
Leu Leu Leu Ala Ala Ala Gly Cys Gly Ser Lys Pro Pro Ser Gly Ser
            20                  25                  30 cct gaa acg ggc gcc ggc gcc ggt act gtc gcg act acc ccc gcg tcg     144
Pro Glu Thr Gly Ala Gly Ala Gly Thr Val Ala Thr Thr Pro Ala Ser
        35                  40                  45 tcg ccg gtg acg ttg gcg gag acc ggt agc acg ctg ctc tac ccg ctg     192
Ser Pro Val Thr Leu Ala Glu Thr Gly Ser Thr Leu Leu Tyr Pro Leu
    50                  55                  60
```

| | | | | | | | | | | | | | | | |
|---|---|---|---|---|---|---|---|---|---|---|---|---|---|---|---|
| ttc | aac | ctg | tgg | ggt | ccg | gcc | ttt | cac | gag | agg | tat | ccg | aac | gtc | acg | 240 |
| Phe | Asn | Leu | Trp | Gly | Pro | Ala | Phe | His | Glu | Arg | Tyr | Pro | Asn | Val | Thr | |
| 65 | | | | 70 | | | | | 75 | | | | | 80 | | |
| atc | acc | gct | cag | ggc | acc | ggt | tct | ggt | gcc | ggg | atc | gcg | cag | gcc | gcc | 288 |
| Ile | Thr | Ala | Gln | Gly | Thr | Gly | Ser | Gly | Ala | Gly | Ile | Ala | Gln | Ala | Ala | |
| | | | | 85 | | | | | 90 | | | | | 95 | | |
| gcc | ggg | acg | gtc | aac | att | ggg | gcc | tcc | gac | gcc | tat | ctg | tcg | gaa | ggt | 336 |
| Ala | Gly | Thr | Val | Asn | Ile | Gly | Ala | Ser | Asp | Ala | Tyr | Leu | Ser | Glu | Gly | |
| | | | 100 | | | | | 105 | | | | | 110 | | | |
| gat | atg | gcc | gcg | cac | aag | ggg | ctg | atg | aac | atc | gcg | cta | gcc | atc | tcc | 384 |
| Asp | Met | Ala | Ala | His | Lys | Gly | Leu | Met | Asn | Ile | Ala | Leu | Ala | Ile | Ser | |
| | | | 115 | | | | | 120 | | | | | 125 | | | |
| gct | cag | cag | gtc | aac | tac | aac | ctg | ccc | gga | gtg | agc | gag | cac | ctc | aag | 432 |
| Ala | Gln | Gln | Val | Asn | Tyr | Asn | Leu | Pro | Gly | Val | Ser | Glu | His | Leu | Lys | |
| | | 130 | | | | | 135 | | | | | 140 | | | | |
| ctg | aac | gga | aaa | gtc | ctg | gcg | gcc | atg | tac | cag | ggc | acc | atc | aaa | acc | 480 |
| Leu | Asn | Gly | Lys | Val | Leu | Ala | Ala | Met | Tyr | Gln | Gly | Thr | Ile | Lys | Thr | |
| 145 | | | | | 150 | | | | | 155 | | | | | 160 | |
| tgg | gac | gac | ccg | cag | atc | gct | gcg | ctc | aac | ccc | ggc | gtg | aac | ctg | ccc | 528 |
| Trp | Asp | Asp | Pro | Gln | Ile | Ala | Ala | Leu | Asn | Pro | Gly | Val | Asn | Leu | Pro | |
| | | | | 165 | | | | | 170 | | | | | 175 | | |
| ggc | acc | gcg | gta | gtt | ccg | ctg | cac | cgc | tcc | gac | ggg | tcc | ggt | gac | acc | 576 |
| Gly | Thr | Ala | Val | Val | Pro | Leu | His | Arg | Ser | Asp | Gly | Ser | Gly | Asp | Thr | |
| | | | 180 | | | | | 185 | | | | | 190 | | | |
| ttc | ttg | ttc | acc | cag | tac | ctg | tcc | aag | caa | gat | ccc | gag | ggc | tgg | ggc | 624 |
| Phe | Leu | Phe | Thr | Gln | Tyr | Leu | Ser | Lys | Gln | Asp | Pro | Glu | Gly | Trp | Gly | |
| | | | 195 | | | | | 200 | | | | | 205 | | | |
| aag | tcg | ccc | ggc | ttc | ggc | acc | acc | gtc | gac | ttc | ccg | gcg | gtg | ccg | ggt | 672 |
| Lys | Ser | Pro | Gly | Phe | Gly | Thr | Thr | Val | Asp | Phe | Pro | Ala | Val | Pro | Gly | |
| | 210 | | | | | 215 | | | | | 220 | | | | | |
| gcg | ctg | ggt | gag | aac | ggc | aac | ggc | ggc | atg | gtg | acc | ggt | tgc | gcc | gag | 720 |
| Ala | Leu | Gly | Glu | Asn | Gly | Asn | Gly | Gly | Met | Val | Thr | Gly | Cys | Ala | Glu | |
| 225 | | | | | 230 | | | | | 235 | | | | | 240 | |
| aca | ccg | ggc | tgc | gtg | gcc | tat | atc | ggc | atc | agc | ttc | ctc | gac | cag | gcc | 768 |
| Thr | Pro | Gly | Cys | Val | Ala | Tyr | Ile | Gly | Ile | Ser | Phe | Leu | Asp | Gln | Ala | |
| | | | | 245 | | | | | 250 | | | | | 255 | | |
| agt | caa | cgg | gga | ctc | ggc | gag | gcc | caa | cta | ggc | aat | agc | tct | ggc | aat | 816 |
| Ser | Gln | Arg | Gly | Leu | Gly | Glu | Ala | Gln | Leu | Gly | Asn | Ser | Ser | Gly | Asn | |
| | | | 260 | | | | | 265 | | | | | 270 | | | |
| ttc | ttg | ttg | ccc | gac | gcg | caa | agc | att | cag | gcc | gcg | gcg | gct | ggc | ttc | 864 |
| Phe | Leu | Leu | Pro | Asp | Ala | Gln | Ser | Ile | Gln | Ala | Ala | Ala | Ala | Gly | Phe | |
| | | 275 | | | | | 280 | | | | | 285 | | | | |
| gca | tcg | aaa | acc | ccg | gcg | aac | cag | gcg | att | tcg | atg | atc | gac | ggg | ccc | 912 |
| Ala | Ser | Lys | Thr | Pro | Ala | Asn | Gln | Ala | Ile | Ser | Met | Ile | Asp | Gly | Pro | |
| | 290 | | | | | 295 | | | | | 300 | | | | | |
| gcc | ccg | gac | ggc | tac | ccg | atc | atc | aac | tac | gag | tac | gcc | atc | gtc | aac | 960 |
| Ala | Pro | Asp | Gly | Tyr | Pro | Ile | Ile | Asn | Tyr | Glu | Tyr | Ala | Ile | Val | Asn | |
| 305 | | | | | 310 | | | | | 315 | | | | | 320 | |
| aac | cgg | caa | aag | gac | gcc | gcc | acc | gcg | cag | acc | ttg | cag | gca | ttt | ctg | 1008 |
| Asn | Arg | Gln | Lys | Asp | Ala | Ala | Thr | Ala | Gln | Thr | Leu | Gln | Ala | Phe | Leu | |
| | | | | 325 | | | | | 330 | | | | | 335 | | |
| cac | tgg | gcg | atc | acc | gac | ggc | aac | aag | gcc | tcg | ttc | ctc | gac | cag | gtt | 1056 |
| His | Trp | Ala | Ile | Thr | Asp | Gly | Asn | Lys | Ala | Ser | Phe | Leu | Asp | Gln | Val | |
| | | | | 340 | | | | | 345 | | | | | 350 | | |
| cat | ttc | cag | ccg | ctg | ccg | ccc | gcg | gtg | gtg | aag | ttg | tct | gac | gcg | ttg | 1104 |
| His | Phe | Gln | Pro | Leu | Pro | Pro | Ala | Val | Val | Lys | Leu | Ser | Asp | Ala | Leu | |
| | | 355 | | | | | 360 | | | | | 365 | | | | |
| atc | gcg | acg | att | tcc | agc | tag | | | | | | | | | | 1125 |
| Ile | Ala | Thr | Ile | Ser | Ser | | | | | | | | | | | |
| | 370 | | | | | | | | | | | | | | | |

<210> SEQ ID NO 2
<211> LENGTH: 374
<212> TYPE: PRT
<213> ORGANISM: Mycobacterium tuberculosis

<400> SEQUENCE: 2

Val Lys Ile Arg Leu His Thr Leu Leu Ala Val Leu Thr Ala Ala Pro
1               5                   10                  15

Leu Leu Leu Ala Ala Gly Cys Gly Ser Lys Pro Pro Ser Gly Ser
            20                  25                  30

Pro Glu Thr Gly Ala Gly Ala Gly Thr Val Ala Thr Thr Pro Ala Ser
            35                  40                  45

Ser Pro Val Thr Leu Ala Glu Thr Gly Ser Thr Leu Leu Tyr Pro Leu
    50                  55                  60

Phe Asn Leu Trp Gly Pro Ala Phe His Glu Arg Tyr Pro Asn Val Thr
65                  70                  75                  80

Ile Thr Ala Gln Gly Thr Gly Ser Gly Ala Gly Ile Ala Gln Ala Ala
                85                  90                  95

Ala Gly Thr Val Asn Ile Gly Ala Ser Asp Ala Tyr Leu Ser Glu Gly
            100                 105                 110

Asp Met Ala Ala His Lys Gly Leu Met Asn Ile Ala Leu Ala Ile Ser
            115                 120                 125

Ala Gln Gln Val Asn Tyr Asn Leu Pro Gly Val Ser Glu His Leu Lys
130                 135                 140

Leu Asn Gly Lys Val Leu Ala Ala Met Tyr Gln Gly Thr Ile Lys Thr
145                 150                 155                 160

Trp Asp Asp Pro Gln Ile Ala Ala Leu Asn Pro Gly Val Asn Leu Pro
                165                 170                 175

Gly Thr Ala Val Val Pro Leu His Arg Ser Asp Gly Ser Gly Asp Thr
            180                 185                 190

Phe Leu Phe Thr Gln Tyr Leu Ser Lys Gln Asp Pro Glu Gly Trp Gly
            195                 200                 205

Lys Ser Pro Gly Phe Gly Thr Thr Val Asp Phe Pro Ala Val Pro Gly
210                 215                 220

Ala Leu Gly Glu Asn Gly Asn Gly Gly Met Val Thr Gly Cys Ala Glu
225                 230                 235                 240

Thr Pro Gly Cys Val Ala Tyr Ile Gly Ile Ser Phe Leu Asp Gln Ala
                245                 250                 255

Ser Gln Arg Gly Leu Gly Glu Ala Gln Leu Gly Asn Ser Ser Gly Asn
            260                 265                 270

Phe Leu Leu Pro Asp Ala Gln Ser Ile Gln Ala Ala Ala Gly Phe
            275                 280                 285

Ala Ser Lys Thr Pro Ala Asn Gln Ala Ile Ser Met Ile Asp Gly Pro
290                 295                 300

Ala Pro Asp Gly Tyr Pro Ile Ile Asn Tyr Glu Tyr Ala Ile Val Asn
305                 310                 315                 320

Asn Arg Gln Lys Asp Ala Ala Thr Ala Gln Thr Leu Gln Ala Phe Leu
                325                 330                 335

His Trp Ala Ile Thr Asp Gly Asn Lys Ala Ser Phe Leu Asp Gln Val
            340                 345                 350

His Phe Gln Pro Leu Pro Pro Ala Val Val Lys Leu Ser Asp Ala Leu
            355                 360                 365

Ile Ala Thr Ile Ser Ser
        370

<210> SEQ ID NO 3
<211> LENGTH: 288
<212> TYPE: DNA
<213> ORGANISM: Mycobacterium tuberculosis
<220> FEATURE:
<221> NAME/KEY: CDS
<222> LOCATION: (1)..(288)

<400> SEQUENCE: 3

```
atg aca gag cag cag tgg aat ttc gcg ggt atc gag gcc gcg gca agc      48
Met Thr Glu Gln Gln Trp Asn Phe Ala Gly Ile Glu Ala Ala Ala Ser
1               5                   10                  15 gca atc cag gga aat gtc acg tcc att cat tcc ctc ctt gac gag ggg      96
Ala Ile Gln Gly Asn Val Thr Ser Ile His Ser Leu Leu Asp Glu Gly
            20                  25                  30 aag cag tcc ctg acc aag ctc gca gcg gcc tgg ggc ggt agc ggt tcg     144
Lys Gln Ser Leu Thr Lys Leu Ala Ala Ala Trp Gly Gly Ser Gly Ser
        35                  40                  45 gag gcg tac cag ggt gtc cag caa aaa tgg gac gcc acg gct acc gag     192
Glu Ala Tyr Gln Gly Val Gln Gln Lys Trp Asp Ala Thr Ala Thr Glu
    50                  55                  60 ctg aac aac gcg ctg cag aac ctg gcg cgg acg atc agc gaa gcc ggt     240
Leu Asn Asn Ala Leu Gln Asn Leu Ala Arg Thr Ile Ser Glu Ala Gly
65                  70                  75                  80 cag gca atg gct tcg acc gaa ggc aac gtc act ggg atg ttc gca tag     288
Gln Ala Met Ala Ser Thr Glu Gly Asn Val Thr Gly Met Phe Ala
                85                  90                  95
```

<210> SEQ ID NO 4
<211> LENGTH: 95
<212> TYPE: PRT
<213> ORGANISM: Mycobacterium tuberculosis

<400> SEQUENCE: 4

```
Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95
```

<210> SEQ ID NO 5
<211> LENGTH: 1428
<212> TYPE: DNA
<213> ORGANISM: Artificial Sequence
<220> FEATURE:
<223> OTHER INFORMATION: Mycobacterium tuberculosis
<220> FEATURE:
<221> NAME/KEY: CDS
<222> LOCATION: (1)..(1428)

<400> SEQUENCE: 5

```
atg gtg aaa att cgt ttg cat acg ctg ttg gcc gtg ttg acc gct gcg      48
Met Val Lys Ile Arg Leu His Thr Leu Leu Ala Val Leu Thr Ala Ala
1               5                   10                  15 ccg ctg ctg cta gca gcg gcg ggc tgt ggc tcg aaa cca ccg agc ggt      96
Pro Leu Leu Leu Ala Ala Ala Gly Cys Gly Ser Lys Pro Pro Ser Gly
```

-continued

| | | | | | | | | | | | | | | |
|---|---|---|---|---|---|---|---|---|---|---|---|---|---|---|
| Pro | Leu | Leu | Leu | Ala | Ala | Ala | Gly | Cys | Gly | Ser | Lys | Pro | Ser | Gly |
| | | 20 | | | | 25 | | | | 30 | | | | |

| tcg | cct | gaa | acg | ggc | gcc | ggc | gcc | ggt | act | gtc | gcg | act | acc | ccc | gcg | 144 |
|---|---|---|---|---|---|---|---|---|---|---|---|---|---|---|---|---|
| Ser | Pro | Glu | Thr | Gly | Ala | Gly | Ala | Gly | Thr | Val | Ala | Thr | Thr | Pro | Ala | |
| | | 35 | | | | 40 | | | | 45 | | | | | | |

| tcg | tcg | ccg | gtg | acg | ttg | gcg | gag | acc | ggt | agc | acg | ctc | ctc | tac | ccg | 192 |
|---|---|---|---|---|---|---|---|---|---|---|---|---|---|---|---|---|
| Ser | Ser | Pro | Val | Thr | Leu | Ala | Glu | Thr | Gly | Ser | Thr | Leu | Leu | Tyr | Pro | |
| | 50 | | | | 55 | | | | 60 | | | | | | | |

| ctg | ttc | aac | ctg | tgg | ggt | ccg | gcc | ttt | cac | gag | agg | tat | ccg | aac | gtc | 240 |
|---|---|---|---|---|---|---|---|---|---|---|---|---|---|---|---|---|
| Leu | Phe | Asn | Leu | Trp | Gly | Pro | Ala | Phe | His | Glu | Arg | Tyr | Pro | Asn | Val | |
| 65 | | | | 70 | | | | 75 | | | | 80 | | | | |

| acg | atc | acc | gct | cag | ggc | acc | ggt | tct | ggt | gcc | ggg | atc | gcg | cag | gcc | 288 |
|---|---|---|---|---|---|---|---|---|---|---|---|---|---|---|---|---|
| Thr | Ile | Thr | Ala | Gln | Gly | Thr | Gly | Ser | Gly | Ala | Gly | Ile | Ala | Gln | Ala | |
| | | | | 85 | | | | 90 | | | | 95 | | | | |

| gcc | gcc | ggg | acg | gtc | aac | att | ggg | gcc | tcc | gac | gcc | tat | ctg | tcg | gaa | 336 |
|---|---|---|---|---|---|---|---|---|---|---|---|---|---|---|---|---|
| Ala | Ala | Gly | Thr | Val | Asn | Ile | Gly | Ala | Ser | Asp | Ala | Tyr | Leu | Ser | Glu | |
| | | | 100 | | | | 105 | | | | 110 | | | | | |

| ggt | gat | atg | gcc | gcg | cac | aag | ggg | ctg | atg | aac | atc | gcg | cta | gcc | atc | 384 |
|---|---|---|---|---|---|---|---|---|---|---|---|---|---|---|---|---|
| Gly | Asp | Met | Ala | Ala | His | Lys | Gly | Leu | Met | Asn | Ile | Ala | Leu | Ala | Ile | |
| | | | 115 | | | | 120 | | | | 125 | | | | | |

| tcc | gct | cag | cag | gtc | aac | tac | aac | ctg | ccc | gga | gtg | agc | gag | cac | ctc | 432 |
|---|---|---|---|---|---|---|---|---|---|---|---|---|---|---|---|---|
| Ser | Ala | Gln | Gln | Val | Asn | Tyr | Asn | Leu | Pro | Gly | Val | Ser | Glu | His | Leu | |
| 130 | | | | | 135 | | | | | 140 | | | | | | |

| aag | ctg | aac | gga | aaa | gtc | ctg | gcg | gcc | atg | tac | cag | ggc | acc | atc | aaa | 480 |
|---|---|---|---|---|---|---|---|---|---|---|---|---|---|---|---|---|
| Lys | Leu | Asn | Gly | Lys | Val | Leu | Ala | Ala | Met | Tyr | Gln | Gly | Thr | Ile | Lys | |
| 145 | | | | | 150 | | | | | 155 | | | | | 160 | |

| acc | tgg | gac | gac | ccg | cag | atc | gct | gcg | ctc | aac | ccc | ggc | gtg | aac | ctg | 528 |
|---|---|---|---|---|---|---|---|---|---|---|---|---|---|---|---|---|
| Thr | Trp | Asp | Asp | Pro | Gln | Ile | Ala | Ala | Leu | Asn | Pro | Gly | Val | Asn | Leu | |
| | | | | 165 | | | | | 170 | | | | | 175 | | |

| ccc | ggc | acc | gcg | gta | gtt | ccg | ctg | cac | cgc | tcc | gac | ggg | tcc | ggt | gac | 576 |
|---|---|---|---|---|---|---|---|---|---|---|---|---|---|---|---|---|
| Pro | Gly | Thr | Ala | Val | Val | Pro | Leu | His | Arg | Ser | Asp | Gly | Ser | Gly | Asp | |
| | | | 180 | | | | | 185 | | | | | 190 | | | |

| acc | ttc | ttg | ttc | acc | cag | tac | ctg | tcc | aag | caa | gat | ccc | gag | ggc | tgg | 624 |
|---|---|---|---|---|---|---|---|---|---|---|---|---|---|---|---|---|
| Thr | Phe | Leu | Phe | Thr | Gln | Tyr | Leu | Ser | Lys | Gln | Asp | Pro | Glu | Gly | Trp | |
| | | 195 | | | | | 200 | | | | | 205 | | | | |

| ggc | aag | tcg | ccc | ggc | ttc | ggc | acc | acc | gtc | gac | ttc | ccg | gcg | gtg | ccg | 672 |
|---|---|---|---|---|---|---|---|---|---|---|---|---|---|---|---|---|
| Gly | Lys | Ser | Pro | Gly | Phe | Gly | Thr | Thr | Val | Asp | Phe | Pro | Ala | Val | Pro | |
| | 210 | | | | | 215 | | | | | 220 | | | | | |

| ggt | gcg | ctg | ggt | gag | aac | ggc | aac | ggc | ggc | atg | gtg | acc | ggt | tgc | gcc | 720 |
|---|---|---|---|---|---|---|---|---|---|---|---|---|---|---|---|---|
| Gly | Ala | Leu | Gly | Glu | Asn | Gly | Asn | Gly | Gly | Met | Val | Thr | Gly | Cys | Ala | |
| 225 | | | | | 230 | | | | | 235 | | | | | 240 | |

| gag | aca | ccg | ggc | tgc | gtg | gcc | tat | atc | ggc | atc | agc | ttc | ctc | gac | cag | 768 |
|---|---|---|---|---|---|---|---|---|---|---|---|---|---|---|---|---|
| Glu | Thr | Pro | Gly | Cys | Val | Ala | Tyr | Ile | Gly | Ile | Ser | Phe | Leu | Asp | Gln | |
| | | | | 245 | | | | | 250 | | | | | 255 | | |

| gcc | agt | caa | cgg | gga | ctc | ggc | gag | gcc | caa | cta | ggc | aat | agc | tct | ggc | 816 |
|---|---|---|---|---|---|---|---|---|---|---|---|---|---|---|---|---|
| Ala | Ser | Gln | Arg | Gly | Leu | Gly | Glu | Ala | Gln | Leu | Gly | Asn | Ser | Ser | Gly | |
| | | | 260 | | | | | 265 | | | | | 270 | | | |

| aat | ttc | ttg | ttg | ccc | gac | gcg | caa | agc | att | cag | gcc | gcg | gcg | gct | ggc | 864 |
|---|---|---|---|---|---|---|---|---|---|---|---|---|---|---|---|---|
| Asn | Phe | Leu | Leu | Pro | Asp | Ala | Gln | Ser | Ile | Gln | Ala | Ala | Ala | Ala | Gly | |
| | | 275 | | | | | 280 | | | | | 285 | | | | |

| ttc | gca | tcg | aaa | acc | ccg | gcg | aac | cag | gcg | att | tcg | atg | atc | gac | ggg | 912 |
|---|---|---|---|---|---|---|---|---|---|---|---|---|---|---|---|---|
| Phe | Ala | Ser | Lys | Thr | Pro | Ala | Asn | Gln | Ala | Ile | Ser | Met | Ile | Asp | Gly | |
| | 290 | | | | | 295 | | | | | 300 | | | | | |

| ccc | gcc | ccg | gac | ggc | tac | ccg | atc | atc | aac | tac | gag | tac | gcc | atc | gtc | 960 |
|---|---|---|---|---|---|---|---|---|---|---|---|---|---|---|---|---|
| Pro | Ala | Pro | Asp | Gly | Tyr | Pro | Ile | Ile | Asn | Tyr | Glu | Tyr | Ala | Ile | Val | |
| 305 | | | | | 310 | | | | | 315 | | | | | 320 | |

| aac | aac | cgg | caa | aag | gac | gcc | gcc | acc | gcg | cag | acc | ttg | cag | gca | ttt | 1008 |
|---|---|---|---|---|---|---|---|---|---|---|---|---|---|---|---|---|
| Asn | Asn | Arg | Gln | Lys | Asp | Ala | Ala | Thr | Ala | Gln | Thr | Leu | Gln | Ala | Phe | |
| | | | | 325 | | | | | 330 | | | | | 335 | | |

| ctg | cac | tgg | gcg | atc | acc | gac | ggc | aac | aag | gcc | tcg | ttc | ctc | gac | cag | 1056 |

```
Leu His Trp Ala Ile Thr Asp Gly Asn Lys Ala Ser Phe Leu Asp Gln
            340                 345                 350 gtt cat ttc cag ccg ctg ccg ccc gcg gtg gtg aag ttg tct gac gcg    1104
Val His Phe Gln Pro Leu Pro Pro Ala Val Val Lys Leu Ser Asp Ala
            355                 360                 365 ttg atc gcg acg att tcc agc gga ggt gga gga tcc atg aca gag cag    1152
Leu Ile Ala Thr Ile Ser Ser Gly Gly Gly Gly Ser Met Thr Glu Gln
            370                 375                 380 cag tgg aat ttc gcg ggt atc gag gcc gcg gca agc gca atc cag gga    1200
Gln Trp Asn Phe Ala Gly Ile Glu Ala Ala Ala Ser Ala Ile Gln Gly
385                 390                 395                 400 aat gtc acg tcc att cat tcc ctc ctt gac gag ggg aag cag tcc ctg    1248
Asn Val Thr Ser Ile His Ser Leu Leu Asp Glu Gly Lys Gln Ser Leu
            405                 410                 415 acc aag ctc gca gcg gcc tgg ggc ggt agc ggt tcg gag gcg tac cag    1296
Thr Lys Leu Ala Ala Ala Trp Gly Gly Ser Gly Ser Glu Ala Tyr Gln
            420                 425                 430 ggt gtc cag caa aaa tgg gac gcc acg gct acc gag ctg aac aac gcg    1344
Gly Val Gln Gln Lys Trp Asp Ala Thr Ala Thr Glu Leu Asn Asn Ala
            435                 440                 445 ctg cag aac ctg gcg cgg acg atc agc gaa gcc ggt cag gca atg gct    1392
Leu Gln Asn Leu Ala Arg Thr Ile Ser Glu Ala Gly Gln Ala Met Ala
    450                 455                 460 tcg acc gaa ggc aac gtc act ggg atg ttc gca taa                    1428
Ser Thr Glu Gly Asn Val Thr Gly Met Phe Ala
465                 470                 475

<210> SEQ ID NO 6
<211> LENGTH: 475
<212> TYPE: PRT
<213> ORGANISM: Artificial Sequence
<220> FEATURE:
<223> OTHER INFORMATION: Synthetic Construct

<400> SEQUENCE: 6

Met Val Lys Ile Arg Leu His Thr Leu Leu Ala Val Leu Thr Ala Ala
1               5                   10                  15

Pro Leu Leu Leu Ala Ala Ala Gly Cys Gly Ser Lys Pro Pro Ser Gly
            20                  25                  30

Ser Pro Glu Thr Gly Ala Gly Ala Gly Thr Val Ala Thr Thr Pro Ala
            35                  40                  45

Ser Ser Pro Val Thr Leu Ala Glu Thr Gly Ser Thr Leu Leu Tyr Pro
    50                  55                  60

Leu Phe Asn Leu Trp Gly Pro Ala Phe His Glu Arg Tyr Pro Asn Val
65                  70                  75                  80

Thr Ile Thr Ala Gln Gly Thr Gly Ser Gly Ala Gly Ile Ala Gln Ala
                85                  90                  95

Ala Ala Gly Thr Val Asn Ile Gly Ala Ser Asp Ala Tyr Leu Ser Glu
            100                 105                 110

Gly Asp Met Ala Ala His Lys Gly Leu Met Asn Ile Ala Leu Ala Ile
            115                 120                 125

Ser Ala Gln Gln Val Asn Tyr Asn Leu Pro Gly Val Ser Glu His Leu
    130                 135                 140

Lys Leu Asn Gly Lys Val Leu Ala Ala Met Tyr Gln Gly Thr Ile Lys
145                 150                 155                 160

Thr Trp Asp Asp Pro Gln Ile Ala Ala Leu Asn Pro Gly Val Asn Leu
                165                 170                 175

Pro Gly Thr Ala Val Val Pro Leu His Arg Ser Asp Gly Ser Gly Asp
            180                 185                 190
```

```
Thr Phe Leu Phe Thr Gln Tyr Leu Ser Lys Gln Asp Pro Glu Gly Trp
            195                 200                 205

Gly Lys Ser Pro Gly Phe Gly Thr Val Asp Phe Pro Ala Val Pro
        210                 215                 220

Gly Ala Leu Gly Glu Asn Gly Asn Gly Gly Met Val Thr Gly Cys Ala
225                 230                 235                 240

Glu Thr Pro Gly Cys Val Ala Tyr Ile Gly Ile Ser Phe Leu Asp Gln
                245                 250                 255

Ala Ser Gln Arg Gly Leu Gly Glu Ala Gln Leu Gly Asn Ser Ser Gly
                260                 265                 270

Asn Phe Leu Pro Asp Ala Gln Ser Ile Gln Ala Ala Ala Gly
            275                 280                 285

Phe Ala Ser Lys Thr Pro Ala Asn Gln Ala Ile Ser Met Ile Asp Gly
            290                 295                 300

Pro Ala Pro Asp Gly Tyr Pro Ile Ile Asn Tyr Glu Tyr Ala Ile Val
305                 310                 315                 320

Asn Asn Arg Gln Lys Asp Ala Ala Thr Ala Gln Thr Leu Gln Ala Phe
                325                 330                 335

Leu His Trp Ala Ile Thr Asp Gly Asn Lys Ala Ser Phe Leu Asp Gln
            340                 345                 350

Val His Phe Gln Pro Leu Pro Pro Ala Val Val Lys Leu Ser Asp Ala
            355                 360                 365

Leu Ile Ala Thr Ile Ser Ser Gly Gly Gly Ser Met Thr Glu Gln
            370                 375                 380

Gln Trp Asn Phe Ala Gly Ile Glu Ala Ala Ala Ser Ala Ile Gln Gly
385                 390                 395                 400

Asn Val Thr Ser Ile His Ser Leu Leu Asp Glu Gly Lys Gln Ser Leu
                405                 410                 415

Thr Lys Leu Ala Ala Ala Trp Gly Gly Ser Gly Ser Glu Ala Tyr Gln
            420                 425                 430

Gly Val Gln Gln Lys Trp Asp Ala Thr Ala Thr Glu Leu Asn Asn Ala
            435                 440                 445

Leu Gln Asn Leu Ala Arg Thr Ile Ser Glu Ala Gly Gln Ala Met Ala
            450                 455                 460

Ser Thr Glu Gly Asn Val Thr Gly Met Phe Ala
465                 470                 475

<210> SEQ ID NO 7
<211> LENGTH: 475
<212> TYPE: PRT
<213> ORGANISM: Artificial Sequence
<220> FEATURE:
<223> OTHER INFORMATION: Mycobacterium tuberculosis
<220> FEATURE:
<221> NAME/KEY: misc_feature
<222> LOCATION: (376)..(380)
<223> OTHER INFORMATION: linker sequence

<400> SEQUENCE: 7

Met Val Lys Ile Arg Leu His Thr Leu Leu Ala Val Leu Thr Ala Ala
1               5

```
Leu Phe Asn Leu Trp Gly Pro Ala Phe His Glu Arg Tyr Pro Asn Val
 65                  70                  75                  80

Thr Ile Thr Ala Gln Gly Thr Gly Ser Gly Ala Gly Ile Ala Gln Ala
                 85                  90                  95

Ala Ala Gly Thr Val Asn Ile Gly Ala Ser Asp Ala Tyr Leu Ser Glu
            100                 105                 110

Gly Asp Met Ala Ala His Lys Gly Leu Met Asn Ile Ala Leu Ala Ile
        115                 120                 125

Ser Ala Gln Gln Val Asn Tyr Asn Leu Pro Gly Val Ser Glu His Leu
130                 135                 140

Lys Leu Asn Gly Lys Val Leu Ala Ala Met Tyr Gln Gly Thr Ile Lys
145                 150                 155                 160

Thr Trp Asp Asp Pro Gln Ile Ala Ala Leu Asn Pro Gly Val Asn Leu
                165                 170                 175

Pro Gly Thr Ala Val Val Pro Leu His Arg Ser Asp Gly Ser Gly Asp
            180                 185                 190

Thr Phe Leu Phe Thr Gln Tyr Leu Ser Lys Gln Asp Pro Glu Gly Trp
        195                 200                 205

Gly Lys Ser Pro Gly Phe Gly Thr Thr Val Asp Phe Pro Ala Val Pro
210                 215                 220

Gly Ala Leu Gly Glu Asn Gly Asn Gly Gly Met Val Thr Gly Cys Ala
225                 230                 235                 240

Glu Thr Pro Gly Cys Val Ala Tyr Ile Gly Ile Ser Phe Leu Asp Gln
                245                 250                 255

Ala Ser Gln Arg Gly Leu Gly Glu Ala Gln Leu Gly Asn Ser Ser Gly
            260                 265                 270

Asn Phe Leu Leu Pro Asp Ala Gln Ser Ile Gln Ala Ala Ala Ala Gly
        275                 280                 285

Phe Ala Ser Lys Thr Pro Ala Asn Gln Ala Ile Ser Met Ile Asp Gly
290                 295                 300

Pro Ala Pro Asp Gly Tyr Pro Ile Ile Asn Tyr Glu Tyr Ala Ile Val
305                 310                 315                 320

Asn Asn Arg Gln Lys Asp Ala Ala Thr Ala Gln Thr Leu Gln Ala Phe
                325                 330                 335

Leu His Trp Ala Ile Thr Asp Gly Asn Lys Ala Ser Phe Leu Asp Gln
            340                 345                 350

Val His Phe Gln Pro Leu Pro Pro Ala Val Val Lys Leu Ser Asp Ala
        355                 360                 365

Leu Ile Ala Thr Ile Ser Ser Gly Gly Gly Ser Met Thr Glu Gln
370                 375                 380

Gln Trp Asn Phe Ala Gly Ile Glu Ala Ala Ala Ser Ala Ile Gln Gly
385                 390                 395                 400

Asn Val Thr Ser Ile His Ser Leu Leu Asp Glu Gly Lys Gln Ser Leu
                405                 410                 415

Thr Lys Leu Ala Ala Ala Trp Gly Gly Ser Gly Ser Glu Ala Tyr Gln
            420                 425                 430

Gly Val Gln Gln Lys Trp Asp Ala Thr Ala Thr Glu Leu Asn Asn Ala
        435                 440                 445

Leu Gln Asn Leu Ala Arg Thr Ile Ser Glu Ala Gly Gln Ala Met Ala
450                 455                 460

Ser Thr Glu Gly Asn Val Thr Gly Met Phe Ala
465                 470                 475
```

```
<210> SEQ ID NO 8
<211> LENGTH: 38
<212> TYPE: DNA
<213> ORGANISM: Artificial Sequence
<220> FEATURE:
<223> OTHER INFORMATION: primer

<400> SEQUENCE: 8
catgccatgg tgaaaattcg tttgcatacg ctgttggc                              38

<210> SEQ ID NO 9
<211> LENGTH: 40
<212> TYPE: DNA
<213> ORGANISM: Artificial Sequence
<220> FEATURE:
<223> OTHER INFORMATION: primer

<400> SEQUENCE: 9
cgggatcctc cacctccgct ggaaatcgtc gcgatcaacg                            40

<210> SEQ ID NO 10
<211> LENGTH: 32
<212> TYPE: DNA
<213> ORGANISM: Artificial Sequence
<220> FEATURE:
<223> OTHER INFORMATION: primer

<400> SEQUENCE: 10
cgggatccat gacagagcag cagtggaatt tc                                    32

<210> SEQ ID NO 11
<211> LENGTH: 33
<212> TYPE: DNA
<213> ORGANISM: Artificial Sequence
<220> FEATURE:
<223> OTHER INFORMATION: primer

<400> SEQUENCE: 11
cccaagctta tgcgaacatc ccagtgacgt tgc                                   33

<210> SEQ ID NO 12
<211> LENGTH: 15
<212> TYPE: DNA
<213> ORGANISM: Artificial Sequence
<220> FEATURE:
<223> OTHER INFORMATION: primer

<400> SEQUENCE: 12
ggaggtggag gatcc                                                       15
```

MYCOBACTERIUM TUBERCULOSIS FUSION PROTEIN AND USES THEREOF

CROSS REFERENCE

This is a divisional application of U.S. patent application Ser. No. 12/160,280 filed Nov. 17, 2008, which was a US National Phase PCT/CN2007/000087 filed Jan. 10, 2007, which claimed the priority of CN200610000710.X filed Jan. 10, 2006, all these applications are incorporated herein by reference.

FIELD OF THE INVENTION

The present invention relates to a genetically engineered *Mycobacterium tuberculosis* fusion protein, and an application of said protein in developing new vaccines for tuberculosis (TB) preventions or immuno-treatments.

BACKGROUND OF THE INVENTION

*Mycobacterium tuberculosis* (*M. tuberculosis*) causes tuberculosis (TB). Each year, about 3 million people around the world are suffering from *M. tuberculosis* induced TB. China is one of the 22 countries around the world that have relatively high level of TB infections. In fact, following India, China has the second largest population of TB patients in the world. Recently, the number of people infected by TB in China is increasing again. According to the 4$^{th}$ nationwide TB epidemiological survey in 2000, China was rated high in several aspects: including the number of people infected (there are up to 550 million people infected, with the infection rate of 45%, which is significantly higher than the average infection level worldwide), the number of patients (there are about 5 million patients with active lung TB), the number of new cases (there are about 1.5 million new cases of active lung TB per year), the fetal rate (which is about 0.2 million per year), and the number of drug-resistant patients (which is around 30% of the patients are drug resistant). We can see from the aforesaid data that the world, especially China, should put in tremendous and imperative effort to control the spread of TB.

TB is an infectious respiratory disease, which is best prevented and controlled by vaccinations. Bacille Calmette Guerin (BCG) is the only TB vaccine so far. BCG is an attenuated vaccine that was discovered by French doctors Calmette and Guerin in 1921. Calmette and Guerin had cultivated 230 generations of *M. bovis* in 13 years before they got an attenuated vaccine successfully. The TB vaccine was named after Calmette and Guerin to memorize their great contributions. Since the technique of reserving bacteria in freezers has yet been developed back then, said bacteria were grown on slanted surface. With other reasons like wars, the originally cultivated strain may have already been lost. Nowadays, several strains are used for BCG production in the world. The one used in China is a strain from Denmark. Vaccinating newborn babies with BCG can prevent severe pediatric TB, like tuberculosis meningitis, and acute military tuberculosis. However, the preventive effect of BCG has not been confirmed (Baily G V, et al, Ind. J. Med. Res., 72:1-74, 1980). Moreover, BCG is useless in protecting those who have already been exposed to *Mycobacteria* in the environment, or who have already been infected by *M. tuberculosis* from TB (Brandt L., et al. Infect. Immun., 70:672-678, 2002). Due to the aforesaid reasons, China has abolished adult BCG vaccination in 2000. To improve the diagnosis of TB, countries with low incidences of TB no longer vaccinate newborn babies with BCG. Since the BCG is an attenuated vaccine, it can not be used to prevent TB from those, such as AIDS patients, who have compromised immune systems, while it is easier for those with compromised immune systems to be infected by *M. tuberculosis*.

In the late 1980s, the number of cases of TB in the United States appeared to be going up again. The international attention was then directed to researches on new TB vaccines, and WHO has founded a TB vaccine research team at the end of last century.

China is an area with relatively large number of TB patients: around 550 million people are infected by *M. tuberculosis*, 10% out of which will develop into TB. By preventing the *M. tuberculosis* infected population from developing into TB, incidences of TB can be lowered, and the control of TB can be achieved more effectively. The high risk population always uses oral Isoniazid for prevention; however, it is usually hard to stick to as patients need to take it for a long time. Moreover, Isoniazid often causes adverse reactions like peripheral neuropathy, and liver damage, as well as special adverse reactions, such as epilepsy, psychonosema, autonomis nervous disorders, etc (Guo L, et al. Chinese Journal of Coal Industry Medicine, 3(9): 940-941, 2000). Therefore, the high risk population needs to be vaccinated for TB prevention, as it is easy, convenient and with little side effects.

Reported TB vaccines can be divided into two general categories: live bacteria vaccine (including live attenuated vaccine, and recombinant BCG) and non-bacteria vaccine (including protein unit vaccine and DNA vaccine). Attenuated vaccines are normally made from bacteria strains that have nutrient defects, for example a strain that has defect in leucine synthesis. The reported fadD26 is a genetically mutated strain of *M. tuberculosis*. The gene product of fadD26 is a chemical similar to acetyl coenzyme A, and it is in charge of phthiocerol dimycocerosates synthesis. Mutations of fadD26 will attenuate *M. tuberculosis* (Infante E, et al. Clinical and Experimental Immunology, 141:21-28, 2005). Since attenuated bacteria strains have the potential of mutating back to its origins (Sampson S L, et al, Infect. Immun., 72:3031-3037, 2004), it is risky to vaccinate those who have compromised immune systems with live attenuated bacteria vaccines. Live attenuated bacteria vaccines may also resemble BCG's fate, namely useless in protecting the infected population. Once DNA vaccines are discovered, since it can stimulate cell immunity, the search for a TB DNA vaccine has become an increasingly hot research topic, and a number of articles have reported DNA vaccines (Sugawara I, et al., Tuberculosis. 83:331-337, 2003). In the process of vaccination by DNA vaccines, encoding genes are incorporated into eukaryotic vectors to construct expression vectors of eukaryotic cell, then using *E. coli* to do plasmid amplification. After the recombined expression vectors of DNA are extracted and strictly purified, naked DNA is injected into muscles for immunity. Various research groups have found that DNA vaccines work safer, more reliable, and better with protein subunit vaccines.

The choice of antigen is absolutely essential in the research of DNA vaccines and protein subunit vaccines. The use of a single kind of antigen does not give ideal results on protecting animals, which are infected by *M. tuberculosis*, from TB, while multiple single proteins or fusion proteins work better than a single kind of antigen. So far, it has been reported that combined antigens, which are cocktails of fusion proteins and multiple antigens, DNA form, recombined proteins, or secreted proteins from the filtered culture of *M. tuberculosis* (Roberts A. D., et al., Immunology, 85: 502-508, 1995). It has also been reported that if protein Ag85B(Rv1886c) and protein ESAT-6(Rv3875) are mixed in the ratio of 1:1 to immune mice, it gives better result than using protein ESAT-6 alone, but it gives worse result than using protein Ag85B alone or using fusion protein Ag85B-EAST-6 (Olsen A W, et al, Infect. Immun., 72:6148-6150, 2004); Ag85B DNA vaccines, MPT64(Rv1980c) DNA vaccines and MPT83(Rv2873) DNA vaccines mixed in the ratio of 1:1:1 to immune cows (Cai H, et al, Vaccine, 23:3887-3895, 2005). If comparing between a single recombinant antigen with fusion protein, as mentioned above, fusion protein has better results than mixing single antigens. Moreover, from the mass production point of view, it is more economical and simple to produce one fusion protein than two recombinant proteins simultaneously. During the past few years, fusion proteins were reported to be used in the research of DNA vaccines, protein subunit vaccines, and recombinant BCG. Fusion proteins mainly include: Ag85B-ESAT-6, ESAT-6-Ab85B, and Mtb72F(mtb39-Ag85B) (Langermans J A M, et al. Vaccine, 23:2740-2750, 2005, Olsen A. W., et al, Infect. Immun., 69: 2773-2778, 2001).

The number of drug-resistant patients in China is huge, which amounts to 30% of the total number of patients. In the past 40 years, there has been no novel TB chemotherapeutic drug on the market; and chemotherapies are facing the problem of consistently high rate of drug resistance. One possible solution to treat drug-resistant patients or hard-to-treat TB patients is to use immuno-therapies to improve chemotherapies. So far, main TB immuno-therapeutic drugs for clinical uses include thymopolypeptides for injection and freeze-dried *M. Vaccae* Vaccine for Therapy-Vaccae. Thymopolypeptides give adverse effects like febris and fever. Non-bacterial vaccine "Vaccae", which is prepared by rupturing *M. Vaccae* cells, has been put onto the market since 2001. It is used for TB immunity treatments mainly, it can also be used to prevent or treat *M. tuberculosis* infections.

Currently, it is urgent to further develop TB vaccines, which have high immunogenicity and small adverse effects, and which can be used for TB immunity treatments. The present invention provides a fusion protein, the expression level of which is 33-38% out of all expressed bacterium proteins. This percentage is significantly higher than the expression level of other current recombinant *M. tuberculosis* fusion proteins in the field, and will fully satisfy the clinical demand. Furthermore, the present invention can significantly stimulate immuno-response directly against *M. tuberculosis*; therefore, it can be used as an antigen to prevent, treat, or diagnose TB, as well as to conduct epidemiological survey and monitoring. The present *M. tuberculosis* fusion protein can be used to prepare new vaccines which can substitute BCG, and therefore provide a new option to prevent or treat TB.

CONTENT OF THE INVENTION

Summary of the Invention

The present invention discloses a *M. tuberculosis* fusion protein, comprising an amino acid sequence shown by SEQ ID NO: 7, or an amino acid sequence obtained by substitution, deletion or addition of one or more amino acids, preferably 1-50, 1-35, 1-25 and 1-15, most preferably 1-5 amino acids in SEQ ID NO: 7. Said fusion protein also possesses the immunogenic activity of *M. tuberculosis* antigen.

The present invention discloses a *M. tuberculosis* fusion protein, having an amino acid sequence shown by SEQ ID NO: 7, or an amino acid sequence obtained by substitution, deletion or addition of one or more amino acids, preferably 1-50, 1-35, 1-25 and 1-15, most preferably 1-5 amino acids in SEQ ID NO: 7. Said fusion protein also possesses the immunogenic activity of *M. tuberculosis* antigen.

In a specific embodiment of the present invention, said fusion protein consists of an amino acid sequence shown by SEQ ID NO: 7.

The present invention involves a nucleic acid sequence coding for said *M. tuberculosis* fusion protein. Said nucleic acid sequence has 80% identity with SEQ ID NO: 5, preferably having 85%, 90%, 95%, 96%, 97%, 98% and 99% identity with SEQ ID No: 5, and the encoded protein has the immunogenic activity of *M. tuberculosis* antigen. Most preferably, the nucleic acid sequence coding for the *M. tuberculosis* fusion protein of the present invention has 100% identity with SEQ ID NO: 5.

The present invention also involves a vector comprising said nucleic acid sequence. A prokaryotic vector is preferred, and the heterozygotic plasmids PET28a-c, PET24a-d, PET30a, PET22b(+) or PET15b are more preferred. In addition, a host cell comprising said nucleic acid sequence or vector is also involved in the present invention. Prokaryotic host cells are preferred, and *E. coli* BL21(DE3) or HMS174 (DE3) are more preferred.

The present invention involves a method for producing said *M. tuberculosis* fusion protein, comprising:
1) preparing an polynucleotide sequence, preferably the polynucleotide sequence shown by SEQ ID NO: 5, coding for the *M. tuberculosis* fusion protein of the present invention;
2) introducing said polynucleotide sequence into a vector, which is preferably selected from the heterozygotic plasmid PET28a-c, PET24a-d, PET30a, PET22b(+) or PET15b;
3) inducing said vector into a host cell, which is preferred to be a prokaryotic host cell, which is more preferred to be *E. coli* BL21(DE3) or HMS174(DE3);
4) culturing said host cell under conditions that facilitate the expression of said polynucleotide sequence; and
5) recovering, purifying, and renaturing said protein.

In an embodiment, said *M. tuberculosis* fusion protein is encoded by a polynucleotide sequence which under stringent conditions, specifically low, moderate and high stringent condition, preferably Under moderately stringent condition, most preferably under high stringent condition, hybrids with the nucleic acid sequence shown by SEQ ID NO: 5, and the encoded *M. tuberculosis* fusion protein possesses the antigenic activity of *M. tuberculosis* antigen.

In a preferred embodiment, the present fusion protein was prepared by a method comprising:
1) preparing the polynucleotide sequence as shown in SEQ ID NO: 5;
2) introducing said polynucleotide sequence into a heterozygotic plasmid selected from PET28a-c, PET24a-d, PET30a, PET22b(+) or PET15b;
3) introducing said plasmid into a host cell, selected from *E. coli* BL21(DE3) or HMS174(DE3);
4) culturing said host cell under conditions that facilitate the expression of said nucleic acid sequence; and
5) recovering, purifying, and renaturing said protein.

The present invention relates to a composition comprising said *M. tuberculosis* fusion protein. The present invention also relates to a kit for diagnosing tuberculosis (TB), an article of manufacture for treating tuberculosis (TB), wherein the kit or article of manufacture comprises said *M. tuberculosis* fusion protein or the composition comprising said *M. tuberculosis* fusion protein.

The present invention also involves a vaccine comprising said *M. tuberculosis* fusion protein, composition comprising *M. tuberculosis* fusion protein, or nucleic acid coding for said

*M. tuberculosis* fusion protein. The vaccine may be a preventive or therapeutic vaccine for tuberculosis. The vaccine includes a protein subunit vaccine, complex vaccine or DNA vaccine.

In an embodiment, the present invention involves a use of said *M. tuberculosis* fusion protein, composition, or nucleic acid coding for said *M. tuberculosis* fusion protein in the prevention or treatment of tuberculosis. For example, they can be used to vaccinate healthy population (including those who have or have not been infected by *M. tuberculosis*) to prevent the onset of TB; or to provide an adjuvant immunotherapy for TB patients received ordinary anti-TB chemotherapies to improve the immunity of the patient. The present invention especially provides preventive or therapeutic uses of said *M. tuberculosis* fusion protein, composition, or nucleic acid for individuals who are not infected by *M. tuberculosis*, individuals who are infected by *M. tuberculosis* but do not yet have the onset of tuberculosis, TB patients who are resistant to anti-TB chemicals, or TB patients who are suffered from prolonged chronic TB. The *M. tuberculosis* fusion protein, composition, and nucleic acid coding for the protein can be used in combination with drugs that ordinarily treat TB, for example first-lined drugs, such as Isoniazid (INH), Streptomycin (SM), Sodium Para-aminosalicylate (PAS); Most commonly used anti-TB drugs for control of tuberculosis, such as Rifampicin (RFP), Kanamycin (KM), Ethambutol (EB); Second-lined anti-TB drugs, such as Pyrazinamide (PZA), Capreomycin (CPM), Ethinamide (1314Th), Thioacetazone (TB1); New anti-TB drugs, e.g. quinolones, such as Ofloxacin, Ciprofloxacin, Sparfloxacin, etc; Derivatives of Rifamycin, such as Rifamdin (RFD), Rifapentine (RFT), Rifabutin (RBU), and CGP Rifamycins that have prolonged effects (e.g. CGP27557, CGP29861); New macrolides, is such as Clarithromycin, Roxithromycin, Azithromycin; β-lactams, such as Amoxicillin-clavulanic acid, Ampicillin-clavulanic acid, Ticarcillin-clavulanic acid; And aminoglycosides, such as Amikacin, anti-TB mixture preparations mixed by several different kinds of drugs in certain ratio, for example, Rifamate capsules that contain INH and RFP, and Rifater tablets that contain INH, RFP and PZA. Said *M. tuberculosis* fusion protein, composition, or nucleic acid coding for said *M. tuberculosis* fusion protein can be administrated with said ordinary anti-TB drug either simultaneously or sequentially.

The present invention involves a novel method for preventing or treating TB, comprising administration of said *M. tuberculosis* fusion proteins, compositions, vaccines, drugs, or nucleic acid coding for said protein to patients in need. For example, they can be used to prevent tuberculosis of healthy individuals who are infected or not infected by *M. tuberculosis*. They can be administrated as an adjuvant therapy to TB patients that are receiving chemotherapies to treat tuberculosis. And they can be administrated to TB patients that are resistant to anti-TB chemicals or TB patients that are suffered from prolonged chronic TB to provide prevention or treatment to tuberculosis.

In the aforesaid methods, the *M. tuberculosis* fusion proteins can be used in combination with other anti-TB chemotherapeutic drugs. Examples of said anti-TB chemotherapeutic drugs include: first-lined drugs, such as Isoniazid (INH), Streptomycin (SM), Sodium Para-aminosalicylate (PAS); Most commonly used anti-TB drugs for control of tuberculosis, such as Rifampicin (RFP), Kanamycin (KM), Ethambutol (EB); Second-lined anti-TB drugs, such as Pyrazinamide (PZA), Capreomycin (CPM), Ethinamide (1314Th), Thioacetazone (TB1); New anti-TB drugs, e.g. quinolones, such as Ofloxacin, Ciprofloxacin, Sparfloxacin, etc; Derivatives of Rifamycin, such as Rifamdin (RFD), Rifapentine (RFT), Rifabutin (RBU), and CGP Rifamycins that have prolonged effects (e.g. CGP27557, CGP29861); New macrolides, such as Clarithromycin, Roxithromycin, Azithromycin; β-lactams, such as Amoxicillin-clavulanic acid, Ampicillin-clavulanic acid, Ticarcillin-clavulanic acid; And aminoglycosides, such as Amikacin, anti-TB mixture preparations mixed by several different kinds of drugs in certain ratio, for example, Rifamate capsules that contain INH and RFP, and Rifater tablets that contain INH, RFP and PZA. Said *M. tuberculosis* fusion protein, composition, or nucleic acid coding for said *M. tuberculosis* fusion protein can be administrated with said anti-TB drug either simultaneously or sequentially.

The present invention also involves a method to diagnose or screen TB comprising skin sensitization test or serum sample test that uses the present fusion protein. In an embodiment, said skin sensitization test is referred as intracutaneous inoculation skin tests that are common in the field, such as the Mantoux test.

The present invention further involves an epidemiological survey and monitoring method using the present fusion protein. For example, screening can be conducted by using Mantoux tests on people. If healthy individuals' skin tests are positive, or strong positive especially, said individuals should be determined as individuals that require epidemiological monitoring. One embodiment of the present invention involves a use of the *M. tuberculosis* fusion protein, the composition, or the nucleic acid that codes for the present protein in the preparation of a medicament or vaccine for TB prevention or treatment. For example, said medicament or vaccine can be used to prevent or treat healthy individuals (including those who are infected or not infected by *M. tuberculosis*), TB patients that are receiving anti-TB chemotherapies, TB patients that are resistant to anti-TB chemicals, or TB patients that are suffered from prolonged chronic TB. Said medicament may also comprises aforesaid anti-TB chemotherapeutic drugs, out of which, Streptomycin (SM), Kanamycin (KM), Isoniazid (INH), Rifampicin (RFP), Rifamdin (RFD), Pyrazinamide (PZA), Ethambutol (EB), Capreomycin (CPM), Sodium Para-aminosalicylate (PAS), quinolones, and etc are preferred.

The present invention also involves a TB diagnostic kit or a TB therapeutic kit comprising the *M. tuberculosis* fusion protein, the composition, or the nucleic acid that codes for the present protein. Said diagnostic kit or therapeutic kit contains a vessel that contain the *M. tuberculosis* fusion protein, the composition, or the nucleic acid that codes for the present protein. Said therapeutic kits may also contain vessels that contain aforesaid anti-TB chemotherapeutic drugs, may also contain an instruction on how to take the *M. tuberculosis* fusion protein, the composition, or the nucleic acid that codes for the present protein with the anti-TB chemotherapeutic drugs simultaneously or consecutively.

DETAILED DESCRIPTION OF THE INVENTION

The present invention involves a fusion protein, comprising an amino acid sequence as shown by SEQ ID NO: 7, or comprising an amino acid sequence which has at least about 80% identity with SEQ ID NO: 7, preferably at least about 85%, at least about 90%, at least about 91%, at least about 92%, at least about 93%, at least about 94%, at least about 95%, at least about 96%, at least about 97%, at least about 98% and at least about 99% identity with SEQ ID NO: 7, and the protein has the immunogenic activity of *M. tuberculosis* antigen. Said percentages of amino acid sequence identity can be determined by using various techniques in the art, for example, they can be obtained from publicly shared computer software, such as BLAST, BLAST-2, ALIGN, ALIGH-2 or Megalign (DNASTAR). Those skilled in the art can define appropriate parameters that can be used to measure the identity between sequences, and can be used in any calculations that may be needed to compare full sequences with maximum counterpoint alignments.

The spatial structure and antigen epitopes of the fusion protein, which has immunogenic activity, of the present invention can be analyzed by web-based software and database that known in the art, for example, it can be analyzed by web-based software SYFPEITHI through database www.expasy.ch. For example, by analyzing epitopes HLA-A*6801 15-mers, HLA-DRB1*0101 15-mers, HLA-DRB1*0301 (DR17) 15-mers, HLA-DRB1*0401(DR4Dw4) 15-mers, HLA-DRB1*0701 15-mers, HLA-DRB1*1101 15-mers, and HLA-DRB1*1501(DR2b) 15-mers of the present protein, it can be found that amino acids around sites 1-32, 53-92, 118-186, 203-293, 321-367, 377-400 and 417-477 of SEQ ID NO: 7 are closely associated with the epitopic configurations of an immunogenic active fusion protein. Therefore, a more preferred fusion protein of the present invention contains at least one, or two, or three, or four, or five or six, or seven aforesaid amino acid sites of SEQ ID NO: 7, or contain at least one, or two, or three, or four, or five or six, or seven aforesaid amino acid sites with conservative substitutions in SEQ ID NO: 7. The most preferred fusion protein of the present invention comprises SEQ ID NO: 7, or consists of SEQ ID NO: 7.

In an embodiment, the present invention provides functional fragments of the M. tuberculosis fusion proteins. For example, comparing to the fusion protein represented by SEQ ID NO: 7, said fragments lack unnecessary amino acid residues in the sense of biological activities required by the fusion protein. Examples of such fragments may be amino acids 33-52, 93-117, 294-320, 187-202, 368-376, or 401-416 of SEQ ID NO: 7.

In an embodiment, the present invention provides functional variants of the fusion protein represented by SEQ ID NO: 7. Variations in both the full length and the aforesaid epitope sites of SEQ ID NO: 7 can be induced by any technologies, for example, by the conservative or unconservative mutation guidelines described in the U.S. Pat. No. 5,364,934. One or more amino acids can also be assessed by sequence analysis that scans amino acids. The preferred scanning amino acids thereof are neutral and relatively small ones. Said scanning amino acids include alanine, glycine, serine, and cysteine. Generally speaking, alanine is the most preferred scanning amino acid, because for one, all side chains except for β-carbons are eliminated; for another, the chance that mutations will alternate the conformation of the main chain is very small (Cunningham and Wells, *Science*, 244: 1081-1085 (1989)). The fact that alanine is the most abundant amino acid also explains why alanine is the most preferred. In addition, alanines are always found in both hidden and exposed spots (Creighton, *The Proteins*, page 7, (W.H. Freeman & Co., N.Y.); Chothia, *J. Mol. Biol.*, 150; 1-14 (1976)). However, if alanine substitution can not produce enough mutants, other amino acids with similar functions can also be used.

Amino acid substitution can occur when one amino acid is substituted by another amino acid with similar structural and/or chemical properties, for example leucine can be substituted by isoleucine, and this is also called conservative amino acid substitution. Insertion or deletion is within the range of 1-5 amino acids. By systematically inserting, deleting or substituting amino acids, and by checking the immunogen activity of M. tuberculosis of the resulting mutants, permitted mutations can be measured.

In a specific embodiment, conservative substitutions during the preparation of the present fusion protein were beneficial. Said conservative substitutions are listed under "examples of substitution", and the preferred ones are listed under "preferred substitutions" in Table 1.

TABLE 1

| Original residues substitutions | Examples of substitutions | Preferred |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe; norleucine | Leu |
| Leu (L) | norleucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; norleucine | Leu |

The present fusion protein comprises epitopes that are capable of eliciting an immuno-response against M. tuberculosis. Said protein also possesses immunogenic activity, and can sufficiently stimulate an immuno-response against M. tuberculosis.

Prior to the present invention, no one had fused the M. tuberculosis 38 KD antigen encoding sequence with ESAT-6 antigen encoding sequence to prepare fusion proteins and TB vaccines. WO2005061534 has disclosed a TB vaccine. Said vaccine was prepared from antigens Ag85B, TB10.4, Ag85A, ORF2c, Rv0287 and other analogs. Among these antigens, different combinations were used to prepare fused peptides and TB vaccines, and the major fusion protein herein was Ag85B-TB10.4. The Chinese patent number CN1793367 has disclosed a recombinant protein which was prepared from Ag85B-MPT64 and Mtb8.4, and could be used in anti-TB therapeutic vaccines. The Chinese patent CN1737153 has disclosed a technical solution of a recombinant BCG, which involved the preparation of a BCG recombinant vaccine by transforming Ag85B, ESAT-6, and IFN-γ to BCG.

From long ago until now, there has been no exact answer given by the academia on whether humoral immunity affects TB immunity. People have been striving to construct vaccines with relatively strong T cell sites. Protein 38 KDa is one of the major proteins inside the capsules of M. tuberculosis, and has relatively stronger B cells sites. ESAT-6 is a protein secreted by M. tuberculosis, and its major task is to stimulate T cell multiplication. It is the present invention that found the fusion protein obtained by fusing the aforesaid two proteins can greatly improve the immuno-response against M. tuberculosis. By administrating this fusion protein to an organism, significantly increased response can be seen not only in cellular immunity, but also in humoral immunity within the organism. Last but not least, the molecular weight of the constructed fusion protein is around 50 KD, which is suitable to express in E. coli.

The aforesaid "immunogenic activity" is referring to a property of an antigen capable of stimulating an organism's immune system to produce antibodies and/or effective lymphatic cell. In response to the stimulation generated by foreign antigens, the organism can produce two categories of immuno-responses: humoral immunity and cellular immunity (Lin X, et al., Modern Cellular and Molecular Immunology, 1-11, 1999). Humoral immunity can be examined by using any kinds of examining techniques in the art, for example, agar double diffusion assay, or ELISA. Cellular immunity can be examined by common techniques in the art, such as experiments on checking lymphatic cell proliferation, transformation, level of cytokines secreted by lymphatic cells, or skin hypersensitivity reactions (Olsen A W, et al, Infect. Immun., 72:6148-6150, 2004).

The technical term "immuno-response" is referring to the reaction of the immune system when foreign substances or microorganisms invade the organism. Under normal circumstances, immuno-responses can be divided into specific and non-specific responses, and these two kinds of responses are closely inter-correlated. Non-specific response is an immediate defense against all kinds of foreign substances or infectious agents. While specific response is a representation of a highly effective defense mechanism against foreign substances, which are highly specific to said foreign substances, and are produced against said substances after a lag phase. Specific immuno-response is vital in protecting individuals against said microbial infections at the same time, also in future, it is vital in determining whether the protected individuals, who have recovered from the specific infection, will be able to defend against the specific infection.

The fusion protein of the present invention is capable of eliciting or promoting immuno-responses against *M. tuberculosis*, and therefore can be used to prepare TB preventive vaccines or TB therapeutic vaccines, such as subunit vaccines, DNA vaccines, or integrated vaccines. Said vaccines can be used to immune individuals without *M. tuberculosis* infection so that said individuals will gain immunity against *M. tuberculosis*; Or given to the individuals, who have been infected by *M. tuberculosis* without the onset of tuberculosis, so that said individuals can be prevented from the onset of TB; Or given to individuals with TB, so that they can assist the treatment of other anti-TB drugs by improving the therapeutic effects, shortening the course of treatment, and alleviating adverse effects of anti-TB drugs.

During an organism's immuno-response against *M. tuberculosis* infections, $CD4^+T$ lymph cells are playing a key and important role. $CD4^+T$ lymph cells can form two kinds of helper T cells under different lymphatic factors, namely the Type 1 Helper T Cells (Th1), and the Type 2 Helper T Cells (Th2). The immuno-response of Th1 encourages macrophages to function against pathogenic microbes and other immunogenic protections; while the immuno-response of Th2 mainly promotes the production of antibodies and humoral immuno-responses. Experiments on mice have demonstrated that the CD4 cells involved in *M. tuberculosis* infection are Th1 cells (Orme I M, et al. J. Infect Dis, 167:1481-1497, 1993; Andersen p, et al. J Immunol, 154:3359-3372, 1995). IFN-γ secreted by Th1 cells can activate macrophages to kill intracellular *M. tuberculosis* (Flesch I E, et al. Infect Immun, 58: 2675-2677, 1990). Macrophages first phagocytose, process, and present antigens of *M. tuberculosis* sequentially, then promote the transformation of mature T cells to different helper T cells under the effect of various lymphatic factors. On one hand, IL-12 produced by macrophages can promote T cell responses that are mainly Th1 cell responses. The major products of Th1 cells are IL-2 and IFN-γ. The IFN-γ secreted by Th1 cell activates macrophages in turn. In response to IFN-γ, macrophages then secrete TNF-α and TGF-β, both of which can induce pathological changes in tuberculoma, and result in immuno-protections. On the other hand, IL-10, which is also produced by macrophages, can promote T cell responses that are mainly Th2 cell responses. The main product of Th2 cells is IL-4, and IL-4 is one of the major lymphatic factors which is capable of eliciting B cell response, and induce humoral immunity (Li Z, et al, A New Generation of Vaccine, 221-222, 2001; Kamath A T, et al, Infect Immun, 67:1702-1707, 1999). Analyses have shown that IFN-γ is playing an important role in the immuno-response against *M. tuberculosis*, and IL-12 can act against TB by activating Th1 to secrete IFN-γ. This phenomenon is also demonstrated by knock-out mice models (Cooper A M, et al. J Exp Med, 178: 2243-2247, 1993; Cooper Am, et al. J Exp Med, 186:39-45, 1997). Researches have shown that β2 microglobulin knock out mice are hypersensitive to *M. tuberculosis* infections, due to lack of $CD8^+$ cell responses (Flynn J L, et al. Proc Natl Acad Sci USA 89: 12013-12017, 1992), while IFN-γ production is required for $CD8^+$ cells to participate in the immuno-protections against *M. tuberculosis* infections (Tascon R E, et al. Infect Immun, 66: 830-834, 1998).

Nitric oxide (NO) also plays a key and important role during the organism's immuno-responses against *M. tuberculosis* infections.

*M. tuberculosis* is a kind of intracellular parasitic bacteria that can be breathed into lungs through the nasal cavity. It resides mainly in macrophages that found inside pulmonary alveoli. *M. tuberculosis* can stimulate macrophages to produce bactericidal active intermediates of oxygen metabolism (namely ROI, which includes $O_2^-$ and $H_2O_2$) and nitrogen metabolism (namely RNI, which includes NO and $NO^-$) (Chan J, et al. Clinical Immunol, 110: 2-12, 2004). IFN-γ and TNF-α can induce the expression of NO synthase, and thereby promote the production of NO, which can then act on microbes inside macrophages (Miller. et al. Infect Immun, 72:2872-2878, 2004). Oka H, et al. (Immunol Letters, 70:109-117, 1999) pointed out that NO can be synthesized from arginines inside pulmonary alveoli macrophages, under the catalysis of NO synthase. NO is a reactive nitrogen intermediate secreted by activated macrophages, and it has strong inhibiting and killing effects on *M. tuberculosis* inside macrophages.

In the present invention, the nucleotide sequence of the fusion protein is referring to nucleotide sequences that are 80% homologous to SEQ ID NO: 5. Nucleotide sequences that are 85%, 90%, 95%, 96%, 97%, 98%, 99% homologous to SEQ ID NO: 5 are increasingly more preferred. Moreover, said nucleotide sequence also possesses the immunogenic activity of *M. tuberculosis* antigen. Among the nucleotide sequences, the most preferred is that with 100% homologous to SEQ ID NO: 5.

In another embodiment, polynucleotides coding for the present fusion protein have immunogenic activities and can hybridize with the nucleotide sequence shown in SEQ ID NO: 5. Polynucleotides which can hybridize under stringent hybridizing and washing conditions, especially moderately stringent hybridizing and washing conditions and highly stringent hybridizing and washing conditions, are preferred.

It is easy for those skilled in the art to determine the "stringency" of a hybridization reaction. Generally, "stringency" can be calculated from the length of the probe, the temperature of washing, and the concentration of salts based on experiences. Generally speaking, the longer the probe, the higher the appropriate annealing temperature needed, and the shorter the probe, the lower the appropriate temperature needed. Hybridization is generally dependent on the reannealing abilities of DNA in the presence of the complimentary chain and at the temperature lower than its melting temperature. The higher the percentage of homology between the probe and the hybridizable sequence, the higher the temperature can be used. As a result, the reacting conditions get increasingly more stringent while the relative temperature increases, conversely, the lower the temperature, the less stringent the reacting condition. For more detailed conditions and explanations regarding said hybridization reaction, please refer to (Ausubel, et al., *Current Protocols in Molecular Biology*, Chapter 7, John Wiley & Sons, Inc. 1999).

"Stringent conditions" or "highly stringent conditions" in the present passage can be defined through the following restrictions: (1) use low ion strength and high temperature to wash, for example, 50° C., 0.015M sodium chloride/0.0015M sodium citrate/0.1% sodium dodecylsulphate; (2) use denaturants, such as methanamide, during the process of hybridization, for example, 50% (v/v) methanamide and 0.1% bovine serum albumin (BSA)/0.1% Ficoll/0.1% polyvidone (PVP)/50 mM sodium phosphate buffer, pH 6.5, contains 750 mM sodium chloride, 75 mM sodium citrate, 42° C., or (3) use 42° C., 50% methanamide, 5×SSC (0.75M NaCl, 0.075M sodium citrate), 50 mM sodium phosphate (pH 6.8), 0.1% sodium pyrophosphate, 5×Denhardt's solution, 50 μg/ml ultrasonically treated salmon sperm DNA, 0.1% SDS, and 10% dentran sulfate. Wash in 42° C. 0.2×SSC (sodium chloride/sodium citrate) and 55° C. 50% methanamide, and then wash in 55° C. EDTA containing 0.1×SSC for highly stringent washes.

"Moderately stringent condition" can follow the description in Sambrook et al, *Molecular Cloning: A Laboratory Manual*, New York: Cold Spring Harbor Press, 2001, and can also comprise the aforesaid descriptions on washing solutions and hybridization conditions (such as, temperature, ionic strength, and % SDS) under less stringent circumstances. An example of moderately stringent conditions is to incubate 20% methanamide, 5×Denhardt's solution, 10% dentran sulfate, and 20 mg/ml denatured and sheared salmon sperm DNA, under 37° C. overnight, and then wash in 37-50° C. 1×SSC. Those skilled in the art will be aware of how to adjust the temperature and the ionic strength to accommodate the needs of other factors such as the length of the probe.

The present invention also provides a method for the production of said *M. tuberculosis* fusion proteins in large scale.

In an embodiment of the present invention, the present invention provided a method to prepare a *M. tuberculosis* fusion protein construct. The construct of said recombinant fusion protein was obtained by ligating genes coding for two proteins through linkers to produce the construct encoding the fusion protein, and then expressing the fused genes in *E. coli*. Said linkers are usually referred to the flexible and foldable polypeptide linkers that made from hydrophobic amino acids. This can ensure the spatial conformation between the two proteins of the fusion protein is formed similar to naturally occurring proteins. The preferred linkers are $(Gly4Ser)_{1-4}$. Ala-Ala can also be used.

A preferred embodiment of the present invention involves the construction of a nucleotide construct of the *M. tuberculosis* fusion protein that shown in SEQ ID NO: 5. The nucleotide sequence shown in SEQ ID NO: 5 can be prepared by using common methods in the art. Preferably, design two pairs of PCR primers based on the encoding sequences of *M. tuberculosis* proteins. The primers preferably are SEQ ID NOS 8 and 9, as well as the primers shown by SEQ ID NOS: 10 and 11, and then clone the nucleotide sequence shown by SEQ ID NO: 5. The nucleic acid sequence is mutated under common methods in the art, for example as detailed below: 1. mutating the base coding for the first amino acid at the N terminal, which results in a change from GTG to ATG; 2. inserting an amino acid with the triple codon GTG between the first and second amino acids; 3. adding a linker Gly-Gly-Gly-Gly-Ser between the two protein coding genes; 4. mutating the stop codon from TAG to TAA. Changes of the structure of a polynucleotide sequence can change or influence the spatial conformation, such as the secondary structure of the nucleic acid, which would consequently affects the expression level of said nucleotide sequence in the host cell. Alternatives of the second base of said inserted codon can also be A, G or C; the third base can also be: A, T, C; and other point mutations may also be incorporated. Linkers can also be $(Gly4Ser)_2$, $(Gly4Ser)_3$, or $(Gly4Ser)_4$. And said linker can be inserted by either N terminal protein coding gene amplification, or C terminal protein coding gene amplification.

The fusion protein can be produced by cloning the nucleotide sequence shown by SEQ ID NO: 5 into an expression vector, which can then be expressed in a host cell transformed by the expression vector. Based on common approaches, nucleic acid molecules comprising cDNA or DNA sequence of the present *M. tuberculosis* fusion protein are included in the expression construct, and then conventional methods are used to transform host cells. Transformation is referring to the action of introducing DNA, which is treated as an extrachromosomal element or have been chromosomally integrated, into an organism, so that said DNA can be duplicated. Based on the choice of host cells, appropriate and standard techniques are employed to transform said cells. The calcium treatment process which involves calcium chloride and which was described in Cohen, S N, et al. PNAS, 69: 2110-2114 (1972) and Mandel M, et al, Journal of Molecular Biology, 53: 159-162 (1970) can usually be used for prokaryotes or other cells that have cell walls.

Usually, prokaryotes are preferred to express the DNA sequence construct in the present invention. Examples of said prokaryotes are *E. coli, bacillus* such as *Bacillus subtilis*, etc. Other bacteria in the Enterobacteriaceae, such as *Salmonella typhimurium* and *Serratia marcesceus*, and bacteria in the *Pseudomonas* can also be used.

Generally speaking, plasmid vectors comprising replicons and regulatory sequences, which are suitable for prokaryotic host cells, can be used with said hosts. However, recombinant expression vectors formed by inserting DNA of the present protein into vector PET28a-c, PET24a-d, PET30a, PET22b (+) or PET15b are preferred. The heterozygotic plasmids resulted from the nucleic acid coding for the fusion protein of the present invention and vector PET28a-c, PET24a-d, PET30a, PET22b(+) or PET15b, have a high level of stability and are beneficial to the expression of the present protein.

The *M. tuberculosis* promoter can not be recognized by *E. coli* RNA polymerase, while T7 bacterial phage RNA polymerase can only recognize promoters of T7 bacterial phages. Therefore, the chosen T7 bacterial phage promoters can only be expressed, when host bacteria that code for T7 bacterial phage RNA polymerase are chosen. Theoretically, any host bacteria comprising (DE3) lysogenic bacteria, and which does not produce T7 bacterial phage RNA polymerase before protein expression, can be chosen. For example, HMS174 (DE3), JM109(DE3), or BL21(DE3) can all express the protein of the present invention effectively. However, HMS174 (DE3) and BL21 (DE3) are more preferred, since these host cells can produce the protein in larger quantity, and they have faster growth rates, both of which are good for improving productivity.

In a more preferred embodiment (please refer to FIG. 1), first of all, the expression construct, which contains polynucleotide sequences from SEQ ID NO: 5 and plasmid PET28a, was prepared, then said construct was transformed to BL21(DE3). After having been induced by IPTG (Sigma, bought from Yao Bei Biology Company) and cultured for 4-5 hours, bacteria were collected. The expression level of the interested protein was measured quantitatively by gel optical density scanning, and the result suggested that the protein of interest took up to 33-38% out of all proteins from the bacterium. The molecular weight of the protein of interest was 48.4 KDa, which was determined by mass spectrometry.

Conventional purification methods can be employed to purify and renature the obtained proteins. Known purification methods include: absorption and desorption that involving ion exchangers, ultracentrifugation, gel filtration, affinity chromatography, or specific purification methods. The purified protein of the present invention can be renatured by using conventional renaturing agents such as dithiothreitol or 2-mercapto-ethanol.

The fusion protein prepared in the present invention can be used as subunit vaccines for TB prevention and treatment. Said subunit vaccines are constructed from active ingredients that possess immunogenic activities. Other ingredients from the pathological microbes, which do not have immunogenic effects, or which may even cause undesired reactions, are basically excluded from said vaccines, so that the result of immunity is improved, and the reverse effect after vaccinations is reduced. Protein subunit vaccines are safer and more reliable.

The present invention also involves DNA vaccines that code for fusion proteins of the present invention. DNA vaccines are linked to eukaryotic vectors through encoding genes; eukaryotic recombinated expression vectors are then constructed; after using E. coli for recombination and plasmid amplification, recombinated expression vectors of DNA are extracted and strictly purified; and finally, naked DNA is injected into muscles for immunity. Examples of eukaryotic vectors during the preparation of DNA vaccines are pJW4303, pVAX, pcDNA3.0, etc.

The procedures of DNA vaccine vector construction and recombined protein vector construction are the same, apart from the actual vectors. During the construction of recombined protein vectors, proteins need to be purified after they are expressed by the host cells such as E. coli, while only plasmid DNA need to be purified directly during the DNA vaccine vector construction.

The encoding genes of the fusion protein of the present invention can also be used to prepare recombinated BCG. Said recombinated BCG is obtained by inserting said genes, which code for the present fusion protein, into vectors, then transfecting BCG with the resulted vectors, and finally expressing said proteins in BCG.

Antigens and fusion antigens that used to prepare DNA vaccines, subunit vaccines, and recombinated BCG can be used interchangeably, however, the vectors are different. For example, Kita Y et al. introduced fusion protein Mtb72f into BCG construct and obtained the recombinated BCG bacteria strain 72frBCG. Said bacteria strain was shown to have similar effects as BCG by protection experiments done on mice and guinea pigs. And experiments on monkeys showed that said bacteria strain has similar protective effects as BCG, and decreased organ damage (Kita Y, et al. Vaccine, 23: 2132-2135, 2005).

The present fusion protein can be used as an ingredient of an complex vaccine, which can be used to immune or treat TB. For example, the protecting effect can be improved by using the present vaccine with multiple antigens or other vaccines either simultaneously or sequentially.

An embodiment of the present invention involves TB preventive or therapeutic vaccine comprising the fusion protein of the present invention or the nucleic acid encoding the fusion protein.

An embodiment of the present invention involves a TB diagnostic kit or a TB therapeutic article of manufacture comprising M. tuberculosis fusion protein. In said diagnostic kit or therapeutic article of manufacture, it was more preferred if the present fusion protein is in the form of dry powders, so that it could be diluted to the required concentration before use. It is also feasible if said protein is in the form of solution. Said diagnostic kit or therapeutic article of manufacture may also include a container and a label on the surface of said container or related to said container. Appropriate containers include bottles, small bottles, syringes, etc., and could be made from various materials such as glass or plastic. Said container contains the fusion protein of the present invention, and on the surface of the container there may be a aseptic mouth (for example, said container may be small bottles with plugs which can be pierced by intradermal injection needles). Said label describes the present M. tuberculosis fusion protein is used to treat or prevent TB, and how to use it for TB diagnosis, or how to use it with other drugs. Apart from that, said diagnostic kit or therapeutic article of manufacture may further contain a second container, a third container, etc. Said containers may contain buffers, such as sterilized water for injection (BWFI), phosphate buffers, Ringer's solution, and glucose solution, or may contain anti-TB chemotherapeutic drugs. Said diagnostic kit or therapeutic article of manufacture may also contain other materials, such as other buffers, diluent agents, filters, needles, syringes, etc, to accommodate customers' requests.

The present M. tuberculosis fusion protein can be used to prepare TB diagnostic or screening kits, which can easily, quickly, and accurately diagnose TB clinically. Furthermore, said kits are even more useful in large scale epidemiological survey and monitoring of TB.

In those kits used for TB detection, the present M. tuberculosis fusion protein can also be tagged or labeled. It can be tagged or labeled with enzymes, fluorescent materials, luminescent materials, radioactive materials, metal chelates, etc. The preferred enzymatic markers include: peroxidase, alkaline phosphatase, β-D-galactosidase, malate dehydrogenase, staphylococcal nuclease, δ-5-steroid isomerase, α-glycerol phosphate dehydrogenase, triglycophosphoric acid isomerase, horseradish peroxidase, asparaginase, glucose oxidase, ribonuclease, urease, hydrogen peroxidase, glucose-6-phosphate dehydrogenase, glucoamylase, acetylcholine esterase, etc. The preferred fluorescent materials include: fluorescein isothiocyanate, phycobiliprotein, rhodamine, phycoerythrin, phycocyanin, allophycocyanin, and o-phthaldialdehyde. The preferred luminescent materials include: isoluminol, lucigenin, luminol, aromatic acridinium ester, imidazole, acridinium salts and its modified esters, luciferin, luciferase, and aequorin. The preferred radioactive materials include: $^{125}I$, $^{127}I$, $^{131}I$, $^{14}C$, $^{3}H$, $^{32}P$, $^{35}S$, etc. The preferred metallic materials include colloidal gold, etc.

Methods of binding to the aforesaid markers are known: it can be done either directly or indirectly. Conventional direct marking method is to covalently link the present protein with markers by using a cross-linking agent. Examples of said cross-linking agents are 1,2-di-maleimidyl benzene, N-succinimidyl 4-(N-maleoylaminomethylene)cyclohexanate, N-succinimidyl 6-maleimido hexanate, 4,4'-dithiopyridine, and other known cross-linking agents. Examples of indirect methods include: combine the present protein with light haptens, such as biotin, dinitrobenzene, pyridoxal, or fluorescamine, and then mark the resulted compound from the previous step indirectly. Avidin and streptavidin can be used as ligands for identification.

When an enzyme is used as a marker, the substrates and color developing reagents of said enzyme can be used to test its activity. When peroxidase is used, $H_2O_2$ can be used as a substrate solution, and 2,2'-amino-di(2-ethyl-benzothiazoline sulphonic acid-6)ammonium salt (ABTS), 5-aminosalicylic acid, ortho-phenylenediamine, 4-aminoantipyrine, or 3,3',5,5'-tetramethyl benzidine, etc., can be used as color developing reagents. When alkaline phosphatases are used, ortho-nitrophenolphosphoric acid, para-nitrophenolphosphoric acid, etc., can be used as substrates. When β-D-galactosidase is used, fluorescein-di-(β-D-galactopyranoside), 4-acylumbelliferyl-β-D-galactopyranoside, etc., can be used as substrates.

The present invention involves a use of reagents and kits comprising the present M. tuberculosis fusion protein. Said reagents and kits can be used to detect TB in individuals, such as suspected patients, population in epidemic areas, or individuals that may have M. tuberculosis infection, by facilitating the diagnosis or screening of suspected patients.

In an embodiment, conventional serological methods were employed to facilitate the laboratory diagnosis of TB. For example, reagents and kits comprising the present M. tuberculosis fusion protein, can be used to detect M. tuberculosis antibodies in serum, cerebrospinal fluid, and other body fluids. Detecting methods for M. tuberculosis antibodies include indirect experiments, for example, antigens of the present M. tuberculosis fusion protein are first absorbed onto solid supports, and then test serum is added. If corresponding antibodies are present, said antibodies will combine with antigens and form antigen-antibody compounds. After washes, enzyme marked anti-antibodies or colloidal gold marked anti-antibodies are added, color is developed, and results are observed. The aforesaid indirect experimental methods include ELISA, dot immunoenzyme filtration assay, dot immunogoldfiltration assay, etc. Otherwise, sandwich methods can be used for serological detection, for example, react a test sample with the present active proteins, which are linked to insoluble supports, and the tagged present proteins; the amount of antibodies among the sandwich compounds can then be detected. Competition experiments can also be used to detect antibodies against M. tuberculosis, for example, tagged anti-M. tuberculosis antibodies can be competing with anti-M. tuberculosis antibodies from samples to react with proteins of the present invention; and the level of anti-M. tuberculosis antibodies in the sample can be determined from the amount of tagged anti-M. tuberculosis antibodies that react with the present protein. The titer of the anti-M. tuberculosis antibodies in the sample higher 1-4 folds, preferably 2-3 folds, more preferably 2 folds than the control is clinically significant as an accessorial way to diagnose tuberculosis, or epidemiologically significant to investigate or monitor tuberculosis.

Any biological samples, such as blood plasma, serum, blood, urine, tissue fluid, cerebrospinal fluid, and other body fluid can be used in the assay involving the present protein, and compositions or kits, as long as the sample contains anti-M. tuberculosis antibodies.

In an embodiment, the present protein also facilitates the diagnosis, epidemiological survey and monitor of TB by conventional intradermally inoculation skin tests. For example, the Mantoux approach can be used, for example, filling sterilized 1 ml deposable syringe with 0.1 ml M. tuberculosis proteins of the present invention, and insert said syringe into skin beside the palm and around ⅓ of the left forearm. The presence of a cutaneous hillock indicates a successful injection. The horizontal and vertical radii of any local red swellings or subcutaneous lumps should be measured in millimeters 24 hours after infection. If the average of said horizontal and vertical radii$\geqq$5 mm, it is positive; if the averaged radius<5 mm or there is no reactions (represented by 0), it is negative. In a TB epidemiological survey, healthy individuals are intradermally inoculated with experimental reagents, and those that are positive or strong positive are the major group that requires monitoring for epidemiological prevention.

Reagents and kits comprising the present M. tuberculosis fusion protein, which are used in the aforesaid serological tests and skin tests, are included in the range of the present invention.

BRIEF DESCRIPTION OF THE DRAWINGS

FIG. 2 shows a DNA sequence diagram. The DNA sequence shown is entirely identical with the designed. First of all, the sequence of the mutation sites and the linkers are correct, and the complementary sequence of the genome is identical with the DNA sequence of the genome. FIG. 2-1 illustrates the sequence of the T7 promoter, the 48th base is the target gene base, and the read sequence is 1-549 bp. FIG. 2-2 shows the sequencing of a 38 KDa T7 terminator, the 67th is the target base, and the read sequence includes BamHI restriction site, linker, and 390-1115 bp. FIG. 2-3 shows the sequencing of T7 terminator, the target gene is on the 60th base, the sequence read include the terminator, 1-285 bp of EAST6 sequence, linker, and 970-1125 bp of 38 KDa gene.

FIG. 3 illustrates the result of a SDS-PAGE which was performed on engineered recombinant bacteria. Said figure shows that said engineered bacteria express recombinant protein, mainly in the form of inclusion bodies, under the induction of IPTG. Said engineered bacteria rarely express recombinant protein without the IPTG induction.

| BAND | VOL | Norm'd Vol(μg) | BAND % |
|------|--------|----------------|--------|
| 1    | 42.50  | 2.91           | NONE   |
| 2    | 55.00  | 3.77           | NONE   |
| 3    | 93.50  | 6.41           | NONE   |
| 4    | 79.50  | 5.45           | NONE   |
| 5    | 562.00 | 38.5           | NONE   |
| 6    | 407.88 | 27.95          | NONE   |
| 7    | 56.00  | 3.82           | NONE   |
| 8    | 103.50 | 8.92           | NONE   |
| 9    | 9.78   | 0.66           | NONE   |
| 10   | 0.00   | 0.00           | NONE   |
| 11   | 0.00   | 0.00           | NONE   |
| 12   | 0.00   | 0.00           | NONE   |
| 13   | 23.50  | 1.61           | NONE   |

Figure 5:
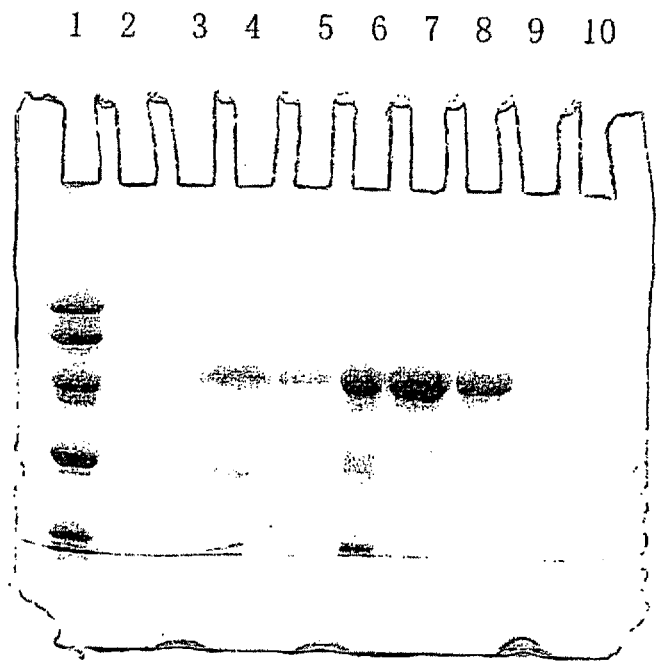

FIG. 5 shows a purification result of the present recombinant protein. Recombinant proteins with relatively higher level of purification can be obtained by filtering solution that contains inclusion bodies through anion column chromatography twice. During the chromatography, the amount of protein used was 10 μg. After said purification, the resulted protein shows a single band on SDS-PAGE.

FIG. 6 shows the amount of IFN-γ secreted by T cells located in mouse spleens in response to the stimulation of the present recombinant protein. Said figure was based on results in Table 7.

EMBODIMENTS

In the following passage, referred embodiments in the present invention will be described in detail. However, these embodiments do not restrict the present invention.

Example 1

The Preparation of *M. tuberculosis* Fusion Proteins

Two pairs of PCR primers were designed based on the Pab sequence of gene 38 KDa(Rv0934) and the gene sequence of ESAT-6(Rv3875). The primer upstream to Pab was 38 bases long, as shown in SEQ ID NO: 8. The protection bases and the NCOI restriction site (including the start, codon ATG) were included in its 5' end design. The primer downstream to Pab was 40 bases long, as shown in SEQ ID NO: 9. The BamHI restriction site and linker were included in its 5' end design. The PCR amplification product of said primers was run through 1.2% agarose gel electrophoresis and the result showed a distinctively amplified band under ultraviolet light. Said band was around 1151 bp, which met the requirements of the design. The primer upstream to ESAT-6 was 32 bases long, as shown in SEQ ID NO: 10. The protection bases and BamHIH restriction site were included in its 5' end design. The primer downstream to ESAT-6 was 33 bases long, as shown in SEQ ID NO: 11. The BamHI restriction site and terminator TAA were included in its 5' end design. The PCR amplification product of said primers was run through 1.2% agarose gel electrophoresis and the result showed a distinctively amplified band under ultraviolet light. Said band was around 300 bp, which met the requirements of the design Said PCR amplification product of the Pab sequence from gene 38 KDa(Rv0934) was mutated: the codon of the first amino acid of the first protein was mutated from GTG to ATG; Val (whose codon is GTG) was inserted between the first and the second amino acids; sequence GGAGGTGGAGGATCC-(SEQ ID NO: 12) was inserted between the sequence encoding the two proteins, and the terminal codon was mutated from TAG to TAA. By using the *M. tuberculosis* H37Rv genome DNA as a template, and Taq PlusI DNA polymerase (from Shanghai Sangon Biological Engineering Technology & Services), PCR was performed, and gene coding for Pab, linker, and gene coding for ESAT-6 were obtained. Said two genes were linked by ligase and became the polynucleotides of the present protein as shown in SEQ ID NO: 5. In said sequence GGAGGTGGAGGATCC (SEQ ID NO: 12), the $3^{rd}$ nucleotide of the codons for $1^{st}$ to $4^{th}$ amino acids could be A, T, G, or C, the codon for the $5^{th}$ amino acid TCC could be mutated to TCT, TCA, TCG, AGT, or AGC.

Figure 1:
FIG. 1 shows a restriction analysis of the recombinant plasmid. After the double digestion of the restriction endonucleases NcoI and HindIII, the fusion expression plasmid shows a target gene fragment of around 1.5 kb and a linear plasmid DNA of around 5.3 kb; double digestion of NcoI and BamHIH results in a ~1.2 kb fragment of the target gene and a linear plasmid DNA of around 5.6 kb; BamHI and HindIII double digestion results in a target gene fragment of around 0.3 kb and a linear plasmid DNA of around 6.5 kb; BamHI single digestion only results in a fragment of around 6.8 kb. After the double digestion of NcoI and BamHI, the recombinant vector of genes which code for N terminal proteins shows a target gene fragment of around 1.2 kb and a linear plasmid DNA of around 5.3 kb; BamHI digestion on the recombinant vector of genes which code for N terminal proteins gives a linear plasmid DNA of around 6.5 kb. The protein coded DNA is successfully ligated with the vector at accurate restriction sites, and the recombinant plasmid contains the fusion gene that expresses the protein. The inserted external gene is also of the same size as the theory suggests.
Figure 3:
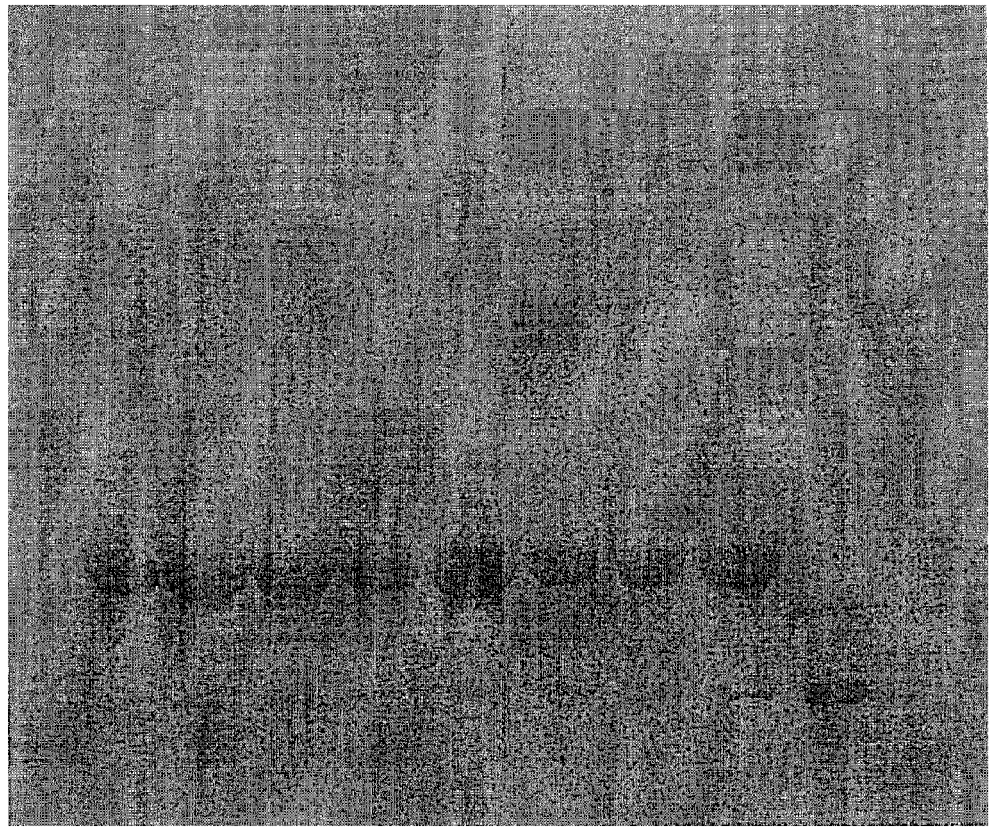
Figure 4:
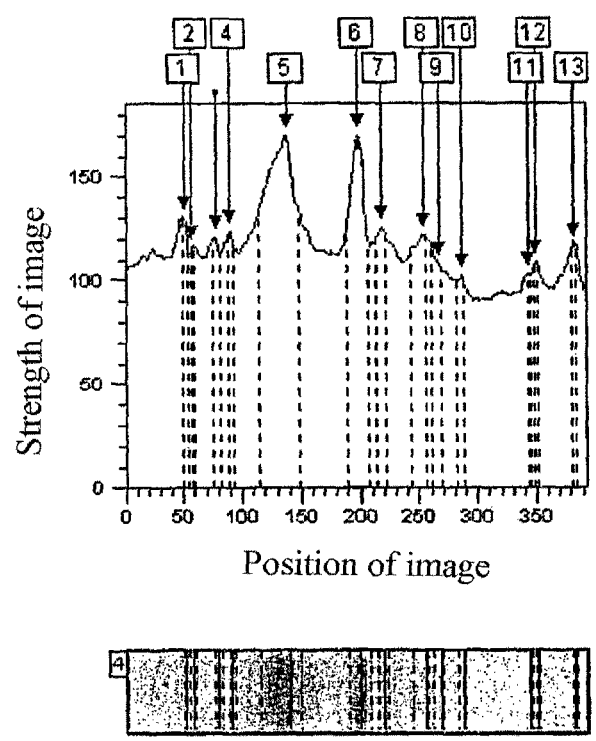
FIG. 4 shows a scan map of all proteins in the bacterium. The 5th band represents the target protein which takes up 38.5% of all proteins of the bacterium. The scanning result is as followed.

The expression vector and PCR amplified Pab with linker were first treated with restriction endonucleases NcoI and BamHI (products of New England Biolab, bought from Friendship Biotechnology Co., Ltd); then separated by 1.0% agarose (products of Sigma, bought from Beijing Dingguo Biotechnology Co., Ltd) gel electrophoresis. After which, bands that contained DNA were cut; and DNA were recovered by following the description of DNA fast purification kit. The recovered polynucleotides and PET28a plasmid expression vector (products of Invitrogen) were ligated by $T_4$ DNA ligase (product of New England Biolabs, bought from Friendship Biotechnology Co., Ltd) to form recombinant heterozygotic plasmids 1 (P38). The recombinant heterozygotic plasmids 1 were then transformed to competent *E. coli* DH5α (bought from Beijing Dingguo Biotechnology Co., Ltd). Colonies of said recombinant *E. coli* were screened and selected against two standards: one, *E. coli* DH5α had recombinant heterozygotic plasmids 1; the other, said plasmids gave same restriction analysis results as shown in FIG. 1 after both single and double restriction digestions. The target gene which was inserted into the recombinant heterozygotic plasmid was sequenced automatically, and proved to be exactly the same as designed. Recombinant heterozygotic plasmids 1 and the ESAT-6 encoding gene were first treated with restriction endonucleases BamHI and HindIII (products of New England Biolabs, bought from Friendship Biotechnology Co., Ltd), and then run through 1.0% agarose gel electrophoresis. After that, bands that contained DNA were cut, and DNA was recovered by following the description of DNA fast purification kit. The recovered polynucleotides and recombinant heterozygotic plasmids 1 were ligated by $T_4$ DNA ligase to form recombinant heterozygotic plasmid 2 (P3810). The recombinant heterozygotic plasmid 2 was then transformed to competent *E. coli* DH5α. Colonies of said recombinant *E. coli* were screened and selected against two standards: one, *E. coli* DH5α had recombinant heterozygotic plasmids 2; the other, said plasmid gave same restriction analysis result as shown in FIG. 1 after both single and double restriction digestions. The target gene which was inserted into the recombinant heterozygotic plasmid 2 was sequenced automatically, and ESAT-6 gene sequence was proved to be exactly the same as designed. Those recombinant heterozygotic plasmids 2 that contained the correct target genes were transformed and expressed in host bacteria BL21(DE3) (bought from Beijing Dingguo Biotechnology Co., Ltd), and said recombinant *E. coli* was cultured under the optical density of 0.6-0.8/hour. After having cultured and induced in 0.5 mmol/L-1 nmol/LIPTG for 4-5 hours, bacteria were collected and the expression level of target proteins were determined by gel optical density scanning. The expression level of the target protein was 30%-38% out of all proteins of the bacterium. Therefore, by altering nucleotide sequences and selecting vectors and host cells, high expression level of the present protein was achieved.

Example 2

Purification, Renaturation and Identification of the M. tuberculosis Fusion Protein of the Present Invention First of all, lysis buffer was added into strains (3 ml of lysis buffer per 1 g of bacteria) to suspend them. Then, ultrasonic treatment with power of 200 W was performed to lyse bacteria. Each interval of ultrasonic treatments was 20 seconds, and 80 times of said treatments were separated with every treatment 20 seconds. Resulting solution from the previous step was then centrifuged under 4° C., 12 000 rpm for 15 minutes, the supernatant was discarded, and the inclusion bodies in the precipitation were washed once with lysis buffers 1% Triton-X100 (product of Sigma, bought from Beijing Jing Ke Hong Da Biotechnology Co., Ltd) and 2% Triton-X100 respectively. 50 mmol/L Tris.Cl/8M urea (pH8.5) was then used to dissolve inclusion bodies under 4° C. until most inclusion bodies were dissolved. The resulted solution was centrifuged under 4° C., and 12 000 rpm for 15 minutes, and the supernatant was collected.

50 mmol/L Tris.Cl/8 M urea (pH8.5) was used to balance an ion exchange column sepharose-FF (product of Amersham Biosciences, bought from Beijing Jing Ke Hong Da Biotechnology Co., Ltd), and the supernatant of the inclusion body solution was introduced to said anion exchange chromatography. Then, 50 mmol/L Tris.Cl/8 M urea (pH8.5) was used to sufficiently wash off unbounded proteins, 0-0.3 M NaCl were used in gradual gradients to elute stepwise, and proteins were collected during elution. Solution from the collecting tubes which were corresponding to each elution peaks was run through SDS-PAGE, and collecting tubes of the target proteins were combined. Said combined solution was dialyzed to get rid of salts and renatured by getting rid of urea.

Renaturation process: 50 mmol/L Tris.Cl/6 urea (pH8.8) was used as buffer, the resulting protein solution from the previous step was dialyzed under 4° C. overnight; then, 50 mmol/L Tris.Cl/3 M urea (pH8.8) buffer was used for dialysis under 4° C. overnight; and 50 mmol/L Tris.Cl (pH8.8) was used for dialysis under 4° C. for two days. Therefore, by gradually lowering urea concentrations of buffers, urea in the proteins was taken away gradually, and renaturation was achieved. The resulting solution from the previous step was run through an anion exchange column, and 0-0.5 M NaCl was used for gradient elution. SDS-PAGE was used to identify elution peaks. Collecting tubes containing relatively more and purer the target protein were combined, and dialyzed to get rid of salts. The purified protein run through SDS-PAGE. Gel optical density scanning showed that the purity of the protein was around 96%, HPLC purity measurements also confirmed that the purity was around 96%.

The peptide mass fingerprinting analysis was done by Proteome Center, Peking Union Medical College. Said analysis showed that positions of lysines and arginines in the resulting polypeptide were correct. The tested amino acids were about 90% identical to the theoretical amino acids. Therefore, said protein was the target protein.

Sequence analysis of N terminal amino acids was done by the Peking University. The 15 amino acids on the N terminal of said protein were methionine (M)—valine (V)—lysine (K)—isoleucine (I)—arginine (R)—leucine (L)—histidine (H)—threonine (T)—leucine (L)—leucine (L)—alanine (A)—valine (V)—leucine (L)—threonine (T)—alanine (A) orderly. The result of N terminal sequence analysis showed that the starting amino acid and codon were correct.

Example 3

The Present M. tuberculosis Fusion Protein Promotes the Proliferation and Transformation of Lymphatic Cells MTT reduction assay was used to measure lymphatic cell transformation: lymphatic cells came from 10 healthy people and 10 patients with active tuberculosis. Heparin was added to prevent blood samples from coagulating. The isolation reagent was added and the resulting solution was centrifuged. lymphatic cells were extracted and diluted with culture media RPMI1640 (product from GIBCO, bought from Beijing Xin Jing Ke Biotechnology Co., Ltd). After dilution, take some solution containing lymphatic cells to dye by trypan blue, and the number of living bacteria was counted under microscopy. Cell concentration was adjusted to $5\times10^6$/ml. 100 μl of cell-suspended solution was added to each well. 100 μl, 100 μl/ml of the fusion protein of the present invention, which was diluted with culture media RPMI1640, was also added to each well. 100 μl of culture media RPMI1640 was added to each control wells. 4 duplicate wells were used for each set. All sets were incubated for 6-7 days under the condition of 37° C., 5% $CO_2$. Then, 120 μl of culture media was discarded from each well, after which, 10 μl of 5 mg/ml MTT (product of AMRESC, bought from Beijing Xin Jing Ke Biotechnology Co., Ltd) was added. Said sets were then incubated at 37° C., 5% $CO_2$ for 4 hours, and then 90 μl solutizer (0.01N HCl—isopropanol) was added, and sets were incubated at 37° C., 5% $CO_2$ again for 2 hours. Optical density (OD) was measured by using 570 nm light, and stimulation index (SI=average of wells with antigens $OD_{570nm}$/average of wells without antigens $OD_{570nm}$) was calculated. The results were listed in Table 1 below.

TABLE 1

Results of the lymphatic cell transformation experiments that involved the fusion protein of the present invention

| Groups | PHA stimulation Transformation of the lymphatic cells (SI) average ± SD | The present protein stimulation Transformation of the lymphatic cells (SI) average ± SD |
|---|---|---|
| Healthy individuals | 1.72(0.2) | 1.33(0.31) |
| TB patients | 1.18(0.1) | 1.22(0.08) |

PHA (product of Sigma, bought from Beijing Xin Jing Ke Biotechnology Co., Ltd) stimulates lymphatic cells to transform. The stimulation index (SI) of 70% of the healthy people and 20% of the TB patients exceeded 1.5 (SI>1.5). The present protein also stimulated transformation of the lymphatic cells, and SI of 31% of the healthy people and 25% of the TB patients exceeded 1.5 (SI>1.5).

There was no significant difference between the protein of the present invention and control PHA in terms of stimulating lymphatic cells from TB patients to transform, while there was a difference in terms of stimulating lymphatic cells from healthy people. To sum up, the recombinant protein of the present invention can effectively stimulate the transformation of lymphatic cells from TB patients.

Example 4

The Application of the Present M. tuberculosis Fusion Protein in Serological Diagnosis 192 serum samples were examined by ELISA. Each well was coated by 0.2-1 µg of the present protein, and coating solution was added into control wells. Coating solution used herein was made from 2.94 g/L $NaHCO_3$ and 1.50 g/L $Na_2CO_3$. After coating for 2 hours, liquid was discarded, and then the plate was washed with PBST for 3 times, each time for 3 minutes. Test serum samples were diluted in 1:100 ratio with sample dilution (PBST that contains 0.1% BSA (product of Spanish, bought from Beijing Hua Lv Yuan Biotechnology Developing Center)). Each well was filled with 100 µl of the diluted serum samples, and placed at 37° C. for 1 hour. The plate was washed as aforesaid method for 3 times. HRP tagged secondary antibody (rabbit-anti-human IgG (bought from Beijing Xin Jing Ke Biotechnology Co., Ltd)) was diluted by sample dilution (PBST that contains 0.1% BSA) according to the requirement. Each well was filled with 100 µl said diluted secondary antibody, placed at 37° C. for an hour. After washing the plate as aforesaid method for 3 times, 100 µl developing solution (DAB dissolved in citric acid and sodium dihydrogen phosphate buffer) was added into each well. And 2 drops of 2M sulphuric acid was added to each well to terminate the reaction. OD of each well around 492 nm was determined by enzyme-labeling instruments. The cut off OD value was 2 standard deviations away from the average OD of the healthy people's serum. OD values that exceeds the cut off are considered positive. Refer to Table 2 for results of the ELISA examination on 192 serum samples.

TABLE 2

Results of the serum examination through ELISA using the recombinant protein of the present invention

| Origin of serum | Number of samples | Positive reaction (sensitivity (%)) | Specificity (%) |
|---|---|---|---|
| Healthy people | 72 | 3(4.2) | 95.8% |
| TB patients | 120 | 84(70.0) | — |
| Positive smears | 60 | 50(83.3) | — |
| Negative smears | 60 | 34(56.7) | — |

Results from the table show that the sensitivity of serum examination on TB patients using the present fusion protein is over 70%, and the specificity over 95%. Therefore, the present protein is beneficial in serological diagnosis.

Example 5

The Preventive Effect of the Present M. tuberculosis Fusion Protein

Mice were used as the experimental animal. The experimental group was injected with the present protein (50 µg/ml, 0.2 ml) and adjuvant (extracts of M. tuberculosis, mainly containing polysaccharides and nucleotides). Negative control group was injected with normal saline, and positive control group was immuned with $5 \times 10^5$ BCG for 3 times with 2-3 weeks intervals. 1-2 months after the last immunity, $5 \times 10^4$-$5 \times 10^5$ living M. tuberculosis H37Rv was injected intravenously. Said mice were killed after 2-4 weeks, and the mice spleens were grinded and cultured in improved L-J media for 3-4 weeks before counting the number of colonies. Refer to Table 3 for results.

TABLE 3

The logarithm results of the isolation rates of M. tuberculosis in mice spleens after immunization by the present invention

| Weeks after challenge | Immunization with the present protein x ± SD | Immunization with BCG (positive control) x ± SD | Negative control x ± SD |
|---|---|---|---|
| 2 | 3.94 ± 0.60* | 3.62 ± 0.52* | 4.98 ± 0.25 |
| 3 | 3.76 ± 0.47* | 2.45 ± 0.89* | 5.30 ± 0.35 |
| 4 | 4.03 ± 0.76* | 3.96 ± 0.60* | 5.56 ± 0.33 |

*represents P < 0.05

The present fusion protein had a significant effect in inhibiting *M. tuberculosis*. There was a significant difference between the logarithmic separation numbers of the experimental group and the negative control group (P<0.05).

Example 6

The Treatment Effect of the Present *M. tuberculosis* Fusion Protein

Mice was intravenously injected with $5\times10^4$-$5\times10^5$ living *M. tuberculosis* H37Rv to prepare for *M. tuberculosis* infection models. The mice of the treatment group were intramuscularly injected with the mixture of the present protein (100 μg/ml, 0.2 ml) and adjuvant (extracts from *M. tuberculosis*, mainly containing polysaccharides and nucleotides). The mice of the chemotherapeutic group were treated with regular short-term chemotherapy. The mice of the chemotherapy+ immunization group were treated with chemotherapeutic and intramuscularly injected with the mixture of the present protein (100 μg/ml, 0.2 ml) and adjuvant (extracts from *M. tuberculosis*, mainly to containing polysaccharides and nucleotides). And the control group was treated with normal saline. After 3 or 4 weeks of treatments, 5 animals were randomly selected from each group and their lungs, livers, spleens and lymphatic nodes were dissected for pathological observations. Intact spleens were grinded, inoculated into improved L-J media, and cultured for 3-4 weeks before counting the number of bacteria colonies. Refer to Table 4 for results.

TABLE 4

The logarithm results of the isolation rates of *M. tuberculosis* in mice spleens after immnotherapy with the present protein

| Weeks of treatment | Treatment with the present protein x ± SD | Chemotherapy + immunization of the present protein(x ± SD) | chemotherapy x ± SD | Control x ± SD |
|---|---|---|---|---|
| 3 | 3.04 ± 0.60* | 2.86 ± 1.03* | 3.15 ± 0.28* | 4.57 ± 0.67 |
| 4 | 3.67 ± 0.57* | 3.12 ± 0.85* | 4.43 ± 0.52* | 5.40 ± 0.48 |

*P < 0.05

The results illustrates that the present protein had a stronger inhibition effect on *M. tuberculosis*, and the effect of the combined therapy (with chemotherapy) was even better. There were significant differences (P<0.05) between logarithmic separation numbers of each experimental groups and the control group respectively.

Example 7

The Present *M. tuberculosis* Fusion Protein Promotes the Secretion of Th1 Cytokines Experimental Animal:

BALB/c mice weighed between 18-20 g. There were 24 mice in each group, half of each sex.

Groupings:

Group A: negative control group was injected with normal saline;

Group B: positive control group was intradermally injected with 0.05 mg BCG (BCG for intradermal injection, products of Shanghai Institute of Biological Products, China National Biotec Group, Catalogue number: 2005031002)

Group C: experimental group was injected with 20 µg/mouse present fusion protein prepared as described in the previous Example.

Immunization Regimens:

50% mice (half from each sex) of each group were immunized twice, while the other 50% mice (half from each sex) were immunized 3 times. There were 2-week-intervals between two consecutive immunities, and the experiments were carried out 4 weeks after the last immunity.

Injection route: 0.2 ml intradermal injection

Detail Process:

Spleen cells cultivation: First, collect blood sample by removing an eye ball, and the kill the mice by disconnecting their cervical spines. After sterilization, spleens of the mice were separated, grinded, and filtered through 200 mesh sieves to prepare spleen cell suspension. Said suspension was centrifuged under low spinning speed, and the precipitated cells were washed with RPMI 1640 twice. 2 ml RPMI 1640 containing 15% attenuated calf serum were added to suspend said cells. Trypan blue was used for staining before counting the number of living cells. The concentration of cells was then adjusted to $2\times10^6$/ml to add to 96-welled cell culture plates, with 100 µl cell suspension each well. Experiments were carried out in triplicates under 37° C., 5% $CO_2$ for 72 hours. Supernatant was extracted and stored at −70° C. for cytokine detections.

Cytokine detection: IFN-γ, IL-12, IL-4, and IL-10 were detected by following the description of the cytokine detection kit (product of R&D Systems). Coated antibodies were diluted to appropriate concentrations, and each well was filled with 100 µl of said antibodies. Plates were left in 4° C. overnight. The coating solution was discarded, and then plates were washed for 3 times, each time for 2 minutes. 300 µl of blocking solution was added to block each plate, which then placed at room temperature for an hour, and then washed following the aforesaid method. After that each well was filled with 100 µl (1:5) diluted samples or standard samples from the kit which was diluted to different concentrations, and placed at room temperature for 2 hours. Plates were washed again following the aforesaid method. And then each well was filled with 100 µl diluted test antibodies (by following the description of the kit), and placed at room temperature for 2 hours. After that, plates were washed following the aforesaid method. And then each well was filled with 100 µl developing substrates, and placed at room temperature for 20 minutes. Finally, 100 µl stop buffer was added, and OD was read at 450 nm/540 nm.

All data was processed using the software package SSPS13.0, and $P<0.05$ was adopted to indicate statistical significance.

TABLE 5

Influences of the present fusion protein on mice spleen T cells' cytokine secretion

| Immunization regimen | Group | Anti-fusion protein IgG | IFN-γ | IL-12 | IL-4 | IL-10 |
|---|---|---|---|---|---|---|
| 2 times | A | 0.03 ± 0.03 | 11.8 ± 7.9 | 4564.9 ± 1236.9 | 58.0 ± 34.6 | 78.8 ± 41.3 |
|  | B | 0.2 ± 0.2 | 12.8 ± 1.03 | 4767.5 ± 1368.8 | 44.6 ± 27.6 | 113.8 ± 87.1 |
|  | C | 0.2 ± 0.2 | 23.3 ± 6.1* | 8405.7 ± 2478.2* | 39.7 ± 26.6* | 141.4 ± 52.8 |
| 3 limes | A | 0.05 ± 0.02 | 11.9 ± 32.4 | 5213.5 ± 1688.4 | 60.9 ± 10.4 | 90.4 ± 27.6 |
|  | B | 0.4 ± 0.2 | 36.5 ± 8.9* | 4046.8 ± 608.3 | 58.7 ± 11.1 | 146.1 ± 37.6 |
|  | C | 0.6 ± 0.2 | 37.2 ± 12.2* | 11497.3 ± 1389.4* | 69.2 ± 9.2 | 160.6 ± 35.5 |

*: $p < 0.05$ (there is a significant difference comparing to the control)

It can be seen from Table 5 that, after having been immunized by the present fusion protein for either twice or 3 times, BALB/c mice spleen T cells were promoted to secrete significantly ($p<0.05$) more IFN-γ and IL-12, comparing to the control. IL-4 synthesis was also significantly ($p<0.05$) reduced comparing to the control, after immunization by the present fusion protein twice. The aforesaid experiments on animals showed that the present fusion protein promoted BALB/c mice spleen cells to secrete IFN-γ and IL-12. Th1 cell response was promoted in particular, and the organism's immuno-response against *M. tuberculosis* was therefore promoted.

Example 8

The Present *M. tuberculosis* Fusion Protein Promotes No Synthesis

Experimental Animal:

BALB/c mice weigh between 18-20 g. There are 24 mice in each group, half of each sex.

Groupings:

Group A: negative control group was injected with normal saline;

Group B: positive control group was intradermally injected with 0.05 mg BCG (BCG for intradermal injection, products of Shanghai Institute of Biological Products, China National Biotec Group, Catalogue number: 2005031002)

Group C: experimental group was injected with 20 µg/mouse present fusion protein, which was prepared as described in the previous Example.

Immunization Regimens:

50% mice (half from each sex) of each group were immunized twice, while the other 50% mice (half from each sex) were immunized 3 times. There were 2-week-intervals between two consecutive immunities, and the experiment was carried out 4 weeks after the last immunity.

Injection route: 0.2 ml intradermal injection
Detail Process:

6% soluble starch broth medium was injected into test mice 3 days before dissection. Before killing by disconnecting cervical spines, the abdominal cavity of each test mouse was injected with 2 ml of irrigating fluid, and was gently massaged. After sterilizing the abdomen, a small cut was performed on the abdomen. A sterilized pipette was used to extract irrigating fluid from the abdominal cavity. Macrophages were obtained by centrifuging fluid obtained from the previous step, suspended with 2 ml RPMI 1640 containing 15% attenuated calf serum, and dyed with trypan blue. The number of living macrophages was counted; the concentration of said cell suspension was adjusted to $4 \times 10^5$ cell/ml, and 1 ml of the adjusted cell suspension was added to each well of a 24-well plate. Experiments were carried out in duplicates. Plates were incubated at a 37° C. 5% $CO_2$ for 3 hours. After that, supernatant was discarded, and cells adhering to the wall were washed twice. After another 72 hours of incubation in a 5% $CO_2$ incubator, supernatant was extracted and stored at −70° C. for NO detection. The negative control group (Group A) was immunized at the same time with Group C in which only normal saline was used for injection. The positive control group (Group B) was injected with BCG, and killed at the same time with Group C.

NO secreted by abdominal macrophages was detected by following the description of the NO detection kit (Catalogue number: S0021) from Beyotime. RPMI 1640 containing 15% attenuated calf serum was used to dilute standard samples (1M $NaNO_2$, catalogue number: S0021-1) provided in said kits. Each well on a 96-well plate was filled with 50 μl diluted standard sample or sample. Then 50 μl Griess Reagent I(catalogue number: S0021-2) and 50 μl Griess Reagent II(catalogue number: S0021-3) were added into each well consecutively. OD was read at 540 nm, and the sample concentration can be calculated based on the standard curve.

All data was processed using the software package SSPS13.0, and $P<0.05$ was adopted to indicate statistical significance.

TABLE 6

Influences of the present fusion protein on mice abdominal macrophages

| Immunization regimen | Group A | Group B | Group C |
| --- | --- | --- | --- |
| 2 times | 4.1 ± 0.9 | 8.5 ± 1.5* | 6.7 ± 1.3* |
| 3 times | 4.8 ± 3.2 | 3.2 ± 3.1 | 2.0 ± 1.1 |

*$p < 0.05$(there is a significant difference comparing to the control)

Table 6 shows that NO synthesized by mice abdominal macrophages increased significantly ($p<0.05$) comparing to the control, after immunization by the present fusion protein twice. It also showed that NO synthesis tended to decrease with the increase of the number of immunization. This proves that, the present fusion protein can promote immuno-responses against *M. tuberculosis* by promoting macrophages to synthesize NO.

Example 9

Influences of the Present *M. tuberculosis* Fusion Protein on IFN-γ Secretion

Vaccines:

The present *M. tuberculosis* fusion protein can be used in TB vaccine research. The half-life of a pure fusion protein is short in vivo, therefore, the fusion protein is always used in combination with an adjuvant to improve the protective function of the vaccine. The present protein and the adjuvant (extract from *M. tuberculosis*, mainly containing polysaccharides and nucleotides) was mixed in 1:1 ratio to prepare for experimental vaccine.

Experimental Animal:

BALB/c mice weigh between 18-20 g. There were 24 mice in each group, half of each sex.

Groupings:

Group A: negative control group was injected with normal saline;

Group B: positive control group was intradermally injected with 0.05 mg BCG (BCG for intradermal injection, products of Shanghai Institute of Biological Products, China National Biotec Group, Catalogue number: 2005031002)

Group C: low dose experimental group (10 µg/mouse)

Group D: relatively low dose experimental group (20 µg/mouse)

Group E: medium dose experimental group (40 µg/mouse)

Group F: high dose experimental group (80 µg/mouse)

Immunization Regimens:

50% mice (half from each sex) of each group were immunized twice, while the other 50% mice (half from each sex) were immunized 3 times. There were 2-week-intervals between two consecutive immunities, and the experiment was carried out 4 weeks after the last immunity.

Injection route: 0.2 ml intradermal injection

Experimental Method:

Blood was sampled from mice before killing them by disconnecting cervical spines. After sterilization, mouse spleens were separated, grinded, and filtered through 200 mesh sieves to prepare spleen cell suspension. Said suspension was centrifuged under low spin speed, and the precipitated cells were washed with RPMI 1640 twice. 2 ml RPMI 1640 containing 15% attenuated calf serum were added to suspend said cells. Trypan blue was used to stain before counting the living cells. The concentration of cells was adjusted to $2\times10^6$/ml and 100 µl cell suspension was added to each well of 96-welled cell culture plate. Experiments were carried out in triplicates at 37° C., 5% $CO_2$ for 72 hours. Supernatant was extracted and stored at −70° C. for cytokine detections.

IFN-γ was detected by following the description of the cytokine detection kit (product of R&D Systems) closely. Coated antibodies were diluted to appropriate concentrations, and each well was filled with 100 µl of said antibodies. Plates were left at 4° C. overnight, and then discard the coating solution, wash the plate 3 times, with each time for 2 minutes. 300 µl of blocking solution was added to block each plate which then placed at room temperature for an hour before washes following the aforesaid method. After that each well was filled with 100 µl (1:5) diluted samples or standard samples from the kit which was diluted to different concentrations, and placed in room temperature for 2 hours. Plates were washed again following the aforesaid method. Then each well was filled with 100 µl diluted test antibodies (by following the description), and placed at room temperature for 2 hours. After that, the plate was washed following the aforesaid method. Then each well was filled with 100 µl developing substrates, and placed at room temperature for 20 minutes. Finally, 100 µl stop buffer was added, and OD was read at 450 nm/540 nm.

TABLE 7

IFN-γ secretion by vaccinated and immunized mice spleen cells

| | | Immunization regimen | |
|---|---|---|---|
| Group | Dose(μg) | 2 times | 3 times |
| A | Normal saline | 11.8 ± 7.9 | 11.9 ± 32.4 |
| B | BCG | 12.8 ± 1.03 | 36.5 ± 8.9* |
| C | 10 | 20.8 ± 4.3 | 52.8 ± 20.6* |
| D | 20 | 25.5 ± 21.0 | 36.8 ± 6.5* |
| E | 40 | 109.9 ± 76.2* | 43.6 ± 25.5* |
| F | 80 | 5.8 ± 5.4* | 60.9 ± 29.9* |

*p < 0.05

Table 7 shows that after immunization twice, only Group E had a significant (p<0.05) difference comparing to Group A. However, after immunization 3 times, all of Group B, C, D, E, and F had significant (p<0.05) differences comparing to Group A. Therefore, the present M. tuberculosis fusion protein vaccine can inhibit M. tuberculosis by promoting T cells to secrete IFN-γ, while the adjuvant could extend the duration of the effect of the fusion protein in the M. tuberculosis fusion protein vaccine.

Example 9

The Safety Evaluation of the Present M. tuberculosis Fusion Protein Vaccine

1. Toxicity Tests on Mice
Source of Mice:
Animal Center, Institute of Genetics and Developmental Biology (IGDB), the Chinese Academy of Sciences (CAS). 70 clean KM mice weigh from 16-20 g were used. Laboratory Animals Qualification (NO 0067869), Animal Administration Number: scxk(京)2002-0006.

Vaccine Preparation:

The present *M. tuberculosis* fusion protein vaccine contains the present *M. tuberculosis* fusion protein (antigen) and adjuvant (extract from *M. tuberculosis*, mainly containing polysaccharides and nucleotides). The ratio was antigen:adjuvant=1:1.5.

Groupings:

Mice were divided into 6 groups. Each group contains 12 mice, half of which were from each sex.

Group A: negative control group was injected with normal saline, volume was as specified in the Experimental method;

Group B: positive control group was injected with 0.05 mg BCG (BCG for intradermal injection, products of Shanghai Institute of Biological Products, China National Biotec Group, Catalogue number: 2005031002)

Group C: low dose experimental group, 0.125 mg/ml antigen was used, volume was as specified in the Experimental method;

Group D: medium dose experimental group 0.25 mg/ml antigen, volume was as specified in the Experimental method;

Group E: high dose experimental group 0.5 mg/ml antigen, volume was as specified in the Experimental method;

Experimental Method:

(1) Mice from each group were tagged with 2,4,6-trinitrophenol. Each of the six mice in a group was tagged distinctively, i.e. it was either tagged on the head, the back, the tail, a fore leg, or a hind leg; or it was not tagged at all.

(2) Each mouse was weighed before injections.

(3) Injection: Mice that had tags on their heads, backs, or tails were injected intraperitoneally with 0.5 ml/mouse. Mice that had tags on their fore legs, hind legs, or that had no tags were injected intramuscularly with 0.2 ml/mouse.

(4) Mice were observed everyday for a week. After that, mice were weighed, and some mice were dissected for organ observations.

Results:

Mice were alive and healthy with weights increased, and their organs were observed to be normal. Refer to Table 8 for more details. Calculating from said initial pharmacodynamic results, the dose for a 50 kg adult is in the range of 10 μg-30 μg, while the highest dose used to inject mice intraperitoneally was 20833-62500 times more.

TABLE 8

| Undue toxicity tests on mice | | | | | | | | | |
|---|---|---|---|---|---|---|---|---|---|
| | | Injection | Weight before | Weight after | Status of the animal | | Organ dissection | | |
| Group | Dose | route | the experiment (g) | a week (g) | Healthy | Dead | Liver | Spleen | Lung |
| A | Normal | Abdominal cavity | 17.6 ± 1.3 | 28.8 ± 4.0 | ✓ | | Normal | Normal | Normal |
| | saline | Muscles | 17.6 ± 1.1 | 27.4 ± 4.5 | ✓ | | Normal | Normal | Normal |
| B | BCG | Abdominal cavity | 17.7 ± 0.9 | 25.6 ± 4.3 | ✓ | | Normal | Normal | Normal |
| | | Muscles | 17.1 ± 0.9 | 25.3 ± 4.8 | ✓ | | Normal | Normal | Normal |
| C | 62.5 μg | Abdominal cavity | 17.8 ± 0.8 | 26.0 ± 4.9 | ✓ | | Normal | Normal | Normal |
| | 25.0 μg | Muscles | 17.5 ± 0.5 | 26.0 ± 5.7 | ✓ | | Normal | Normal | Normal |
| D | 125.0 μg | Abdominal cavity | 18.1 ± 0.5 | 26.7 ± 3.0 | ✓ | | Normal | Normal | Normal |
| | 50.0 μg | Muscles | 17.9 ± 0.8 | 26.4 ± 4.8 | ✓ | | Normal | Normal | Normal |
| E | 250.0 μg | Abdominal cavity | 17.4 ± 0.8 | 26.3 ± 2.9 | ✓ | | Normal | Normal | Normal |
| | 100 μg | Muscles | 17.6 ± 1.3 | 26.8 ± 4.8 | ✓ | | Normal | Normal | Normal |

2. Anaphylactic Responses in Guinea Pigs
Experimental Animal:
There are 30 guinea pigs weighed 300-400 g, half from each sex. There are 6 of said guinea pigs in each group. Half of the group was from each sex.
Vaccine preparation: same as the aforesaid method.
Groupings:
Group A: solvent
Group B: positive control group
Group C: low dose vaccine group (100 μg/ml)
Group D: medium dose vaccine group (200 μg/ml)
Group E: high dose vaccine group (1 mg/ml)
Experimental Method:
1. PPD skin tests were conducted on animals before purchase, only those tested negative in PPD skin tests would continue with the following experiments.
2. Guinea pigs were grouped, weighed, and tagged.
3. 0.5 ml was injected intraperitoneally into each guinea pig every other day for 4 times. 14 days after the last injection, said guinea pigs were excited by injecting 1 ml intravenously, so that the excitation dose was 4 times more than the normal injection dose. Responses of the animals were observed for 30 minutes. However, if there were anaphylactic responses, observations would continue till animals returned normal.
Results:
Refer to Table 9. Anaphylactic responses were referred to the events in which the response levels were above++ (including++). Over 50% of the guinea pigs from the high dose group had shown anaphylactic responses.

TABLE 9

Anaphylactic responses in guinea pigs

| Group | Dose | Averaged weight (g) | | | Reaction level (number of guinea pigs) | | | | |
|---|---|---|---|---|---|---|---|---|---|
| | | Before the experiment | Sensitized upon the last injection | During excitation | − | + | ++ | +++ | ++++ |
| A | Solvent | 341.2 ± 14.2 | 387.6 ± 20.8 | 453.5 ± 12.3 | 5 | 1 | 0 | 0 | 0 |
| B | Bovine serum albumin (BSA) | 349.6 ± 15.7 | 380.6 ± 23.6 | 447.1 ± 41.4 | 3 | 0 | 0 | 3 | 0 |
| C | Low dose (50 μg) | 357.1 ± 26.7 | 320.5 ± 69.2 | 447.6 ± 29.5 | 6 | 0 | 0 | 0 | 0 |
| C | Medium dose (100 μg) | 341.4 ± 21.9 | 375.4 ± 15.7 | 439.9 ± 18.4 | 3 | 2 | 1 | 0 | 0 |
| D | High dose (500 μg) | 336.7 ± 51.8 | 354.3 ± 12.7 | 421.2 ± 27.6 | 1 | 2 | 1 | 2 | 0 |

The aforesaid undue toxicity tests on mice and anaphylactic response tests on guinea pigs initially demonstrate that it is relatively safe to use the present fusion protein in animal experiments.

The invention claimed is:

1. A polynucleotide encoding an *M. tuberculosis* fusion protein comprising a nucleic acid sequence having 95% identity with SEQ ID NO: 5, wherein the fusion protein possesses immunogenic activity of *M. tuberculosis* antigen.

2. A vector comprising the polynucleotide of claim 1.

3. The vector of claim 2, which is selected from the group consisting of Heterozygotic plasmids PET28a-c, PET24a-d, PET30a, PET22b(+) and PET15b.

4. A prokaryotic host cell comprising the vector of claim 3.

5. The prokaryotic host cell of claim 4, which is selected from the group consisting of *E. coli* BL21(DE3) and HMS174 (DE3).

6. A method for preparing an *M. tuberculosis* fusion protein comprising a nucleic acid sequence having 95% identity with SEQ ID NO: 5, wherein the fusion protein possesses immunogenic activity of *M. tuberculosis* antigen, comprising:

1) preparing the polynucleotide sequence of claim 1;

2) introducing said polynucleotide sequence into a vector, selected from the group consisting of the heterozygotic plasmids PET28a-c, PET24a-d, PET30a, PET22b(+) and PET15b;

3) introducing said vector into a prokaryotic host cell, selected from the group consisting of *E. coli* BL21(DE3) and HMS174(DE3);

4) culturing said host cell under conditions that facilitate the expression of said polynucleotide sequence; and 5) recovering, purifying, and renaturing said protein.

7. The method of claim 6, wherein the polynucleotide sequence is a sequence shown by SEQ ID NO: 3.

* * * * *

UNITED STATES PATENT AND TRADEMARK OFFICE
CERTIFICATE OF CORRECTION

| | | |
|---|---|---|
| PATENT NO. | : 8,445,662 B2 | Page 1 of 1 |
| APPLICATION NO. | : 13/446098 | |
| DATED | : May 21, 2013 | |
| INVENTOR(S) | : Xiuyun He et al. | |

It is certified that error appears in the above-identified patent and that said Letters Patent is hereby corrected as shown below:

In the Claims:

Col. 46, line 64 should read as follows

Claim --7. The method of claim 6, wherein the polynucleotide sequence is a sequence shown by SEQ ID NO: 5.--

Signed and Sealed this
Thirteenth Day of August, 2013

Teresa Stanek Rea
*Acting Director of the United States Patent and Trademark Office*